US011242559B2

(12) United States Patent
Lo et al.

(10) Patent No.: US 11,242,559 B2
(45) Date of Patent: Feb. 8, 2022

(54) METHOD OF NUCLEAR DNA AND MITOCHONDRIAL DNA ANALYSIS

(71) Applicant: The Chinese University of Hong Kong, Shatin (CN)

(72) Inventors: Yuk-Ming Dennis Lo, Homantin (CN); Rossa Wai Kwun Chiu, Shatin (CN); Kwan Chee Chan, Shatin (CN); Peiyong Jiang, Shatin (CN)

(73) Assignee: The Chinese University of Hong Kong, Shatin (HK)

( * ) Notice: Subject to any disclaimer, the term of this patent is extended or adjusted under 35 U.S.C. 154(b) by 1168 days.

(21) Appl. No.: 14/993,954

(22) Filed: Jan. 12, 2016

(65) Prior Publication Data
US 2016/0203260 A1    Jul. 14, 2016

Related U.S. Application Data

(60) Provisional application No. 62/111,524, filed on Feb. 3, 2015, provisional application No. 62/102,867, filed on Jan. 13, 2015.

(51) Int. Cl.
| | |
|---|---|
| *C12Q 1/6874* | (2018.01) |
| *C12Q 1/6869* | (2018.01) |
| *C12Q 1/6883* | (2018.01) |
| *G16B 40/00* | (2019.01) |
| *C12Q 1/6886* | (2018.01) |
| *G16B 20/20* | (2019.01) |
| *G16B 20/00* | (2019.01) |

(52) U.S. Cl.
CPC ......... *C12Q 1/6874* (2013.01); *C12Q 1/6869* (2013.01); *C12Q 1/6883* (2013.01); *C12Q 1/6886* (2013.01); *G16B 20/20* (2019.02); *G16B 40/00* (2019.02); *G16B 20/00* (2019.02)

(58) Field of Classification Search
None
See application file for complete search history.

(56) References Cited

U.S. PATENT DOCUMENTS

| | | |
|---|---|---|
| 8,741,811 B2 | 6/2014 | Lo et al. |
| 9,121,069 B2 | 9/2015 | Lo et al. |
| 2009/0317814 A1 | 12/2009 | Penning et al. |
| 2013/0237431 A1 | 9/2013 | Lo et al. |
| 2014/0080715 A1 | 3/2014 | Lo et al. |
| 2015/0056619 A1 | 2/2015 | Li et al. |
| 2017/0240975 A1* | 8/2017 | Thierry ............... C12Q 1/6886 |

FOREIGN PATENT DOCUMENTS

| | | |
|---|---|---|
| CN | 104694384 A | 6/2015 |
| WO | 9615263 A1 | 5/1996 |
| WO | 2004005539 A1 | 1/2004 |
| WO | 2012146783 A1 | 11/2012 |
| WO | 2013149385 A1 | 10/2013 |
| WO | 2013188846 A1 | 12/2013 |

OTHER PUBLICATIONS

Chiu et al. (BMJ, 2011;342:c7401, pp. 1-9) (Year: 2011).*
Schwarzenbach et al.(Nature Reviews Cancer, 2011, vol. 11, pp. 426-437) (Year: 2011).*
Kohler et al. (Molecular Cancer 2009, 8:105, pp. 1-8) (Year: 2009).*
Parr et al. (Human Genomics. vol 2. No. 4. 252-257 Jan. 2006) (Year: 2006).*
Beck et al. (Journal of Clinical Oncology 31, No. 15 suppl; pp. 11013-11013; Published online May 20, 2013). (Year: 2013).*
Schutz et al. (Journal of Clinical Oncology 31, No. 15 suppl; pp. 5072-5072; Published online May 20, 2013). (Year: 2013).*
Communication pursuant to Article 94(3) EPC dated Oct. 11, 2018 in EP Patent Application No. 16737076.6. 8 pages.
Supplementary European Search Report dated Dec. 8, 2017 in EP 16737076.6, 13 pages.
Kohler, et al., "Levels of plasma circulating cell free nuclear and mitochondrial DNA as potential biomarkers for breast tumors," Molecular Cancer, 2009, 8:105, pp. 1-8.
Mehra, et al., "Circulating Mitochondrial Nucleic Acids Have Prognostic Value for Survival in Patients with Advanced Prostate Cancer," Clin Cancer Res 2007, 13, 421-426.
Castle, et al., "DNA copy number including telomeres and mitochondria, assayed using next-generation sequencing," BMC Genomics 2010, 11:244, pp. 1-11.
Ye, et al., "High-throughput seguencing in mitochondrial DNA research," Mitochondrion 2014, 17, pp. 157-163.
Jiang, et al., "Increased Mitochondrial DNA Content in Saliva Associated with Head and Neck Cancer," Clinical Cancer Res, 2005, 11, pp. 2486-2491.
Zhao, et al., "Association of mitochondrial DNA content in peripheral blood leukocyte with hepatitis B virus-related hepatocellular carcinoma in a Chinese Han population," Cancer Science, 2011, vol. 102, No. 8, pp. 1553-1558.
Jiang, et al., "Lengthening and shortening of plasma DNA in hepatocellular carcinoma patients," Proceedings of the National Academy of Sciences of the United States of America, 2015, 112 (11) E1317-E1325.

(Continued)

*Primary Examiner* — Pablo S Whaley
(74) *Attorney, Agent, or Firm* — Kilpatrick Townsend & Stockton LLP

(57) ABSTRACT

An amount of mitochondrial DNA molecules relative to an amount of nuclear DNA molecules is determined in a biological sample, and the relative amount is used for various purposes, e.g., screening, detection, prognostication or monitoring of various physiological and pathological conditions. As examples, an amount of mitochondrial DNA can be used to estimate a concentration of DNA of a tissue type, such as a fetal DNA concentration, tumor DNA concentration, or a concentration of DNA in the biological sample derived from a non-hematopoietic tissue source. Sequencing techniques can be used to determine a mitochondrial DNA concentration in a sample for an accurate detection of a level of cancer. A level of an auto-immune disease is also determined using a relative amount of mitochondrial DNA molecules compared nuclear DNA molecules.

16 Claims, 28 Drawing Sheets

(56) References Cited

OTHER PUBLICATIONS

Takeuchi, Hiroya et al.; "Detection of Mitochondrial DNA Alterations in Plasma of Malignant Melanoma Patients"; 2004; Annals of the New York Academy of Sciences; 1022: 50-54; 5 pages.
Mehra, Niven et al.; "Circulating Mitochondrial Nucleic Acids Have Prognostic Value for Survival in Patients with Advanced Prostrate Cancer"; Clinical Cancer Research; 2007; 13(2); pp. 421-426; 7 pages.
He, Yiping et al.; "Heteroplasmic mitochondrial DNA mutations in normal and tumour cells"; Nature; 2010; vol. 464; pp. 610-614; 7 pages.
Strelkova, I.Y. et al.; "Share of extracellular mitochondrial DNA with a mutations increases in the plasma of patients lung cancer after radiotherapy"; Biomeditsinskaya khimiya; 2010; vol. 56, Issue 4; pp. 517-525.
Yu, Man; "Circulating cell-free mitochondrial DNA as a novel cancer biomarker: opportunities and challenges"; Mitochondrial DNA; 2012; 23(5); pp. 329-332.
Nomoto, Shuji et al.; "Mitochondrial D-loop Mutations as Clonal Markers in Multicentric Hepatocellular Carcinoma and Plasma"; Clinical Cancer Research 2002; vol. 8; pp. 481-487.
Zachariah, Rebecca R. et al.; "Levels of Circulating Cell-Free Nuclear and Mitochondrial DNA in Benign and Malignant Ovarian Tumors"; Obstetrics & Gynecology; 2008; vol. 112, No. 4; pp. 843-850.
Shen, Fan et al.; "Association of 5-Methylcytosine and 5-Hydroxymethylcytosine with Mitochondrial DNA Content and Clinical and Biochemical Parameters in Hepatocellular Carcinoma"; PLOS ONE; 2013; vol. 8, Issue 10; e76967; 8 pages.
Jeronimo, Carmen et al.; "Mitochondrial mutations in early stage prostate cancer and bodily fluids"; Oncogene; 2001; 20; pp. 5195-5198.
Cai, Feng Feng et al.; "Mutations of Mitochondrial DNA as Potential Biomarkers in Breast Cancer"; Anticancer Research; 2011; vol. 31, No. 12; pp. 4267-4271.
Choudhuri, Sharmistha et al.; "A repertoire of biomarkers helps in detection and assessment of therapeutic response in epithelial ovarian cancer"; Molecular and Cellular Biochemistry; 2014; 386; pp. 259-269.
Huang, Chu-Yun et al.; "Circulating free mitochondrial DNA concentration and its association with erlotinib treatment in patients with adenocarcinoma of the lung"; Oncology Letters; 2014; 7; pp. 2180-2184.
Chiu, Rossa W.K. et al.; "Quantitative Analysis of Circulating Mitochondrial DNA in Plasma"; Clinical Chemistry; 2003; vol. 49, Issue 5; pp. 719-726.
International Search Report and Written Opinion dated Apr. 19, 2016 in PCT Application No. PCT/CN2016/070786. 12 pages.
Kohler, Corina et al.; "Levels of plasma circulating cell free nuclear and mitochondrial DNA as potential biomarkers for breast tumors"; 2009; Molecular Cancer; 8:105; 8 pages.
Communication pursuant to Article 94(3) EPC dated Sep. 30, 2020 in EP Patent Application No. 16737076.6. 7 pages.
Partial English translation of Office Action dated Dec. 2, 2020 in CN Patent Application No. 201680005411.7. 3 pages.

* cited by examiner

| Tissue | No. of mitochondria per cell | Reference |
|---|---|---|
| Blood cells | 47±17 | Jonas et al. Hum Genet 2014;133:1149-59 |
| Liver | 6000±500 | Yin et al. Br J Cancer 2004;90:2390-6 |
| Breast | 688±389 | Bai et al. J Oncol 2011;2011:496189 |
| Placenta | 412±117 | Qiu et al. Clin Lab 2013;59:655-60. |
| Colon | 154± 26 | Cui et al. BMC Cancer 2013;13:110 |
| Gastric tissues | 4±2 | Zhang et al. Diagn Pathol 2013; 8:173 |
| Skeletal muscle | 3650±620 | Miller et al. Nucleic Acids Res. 2003;31:e61 |
| Heart | 6970±920 | Miller et al. Nucleic Acids Res. 2003;31:e61 |

FIG. 1

METHOD OF NUCLEAR DNA AND MITOCHONDRIAL DNA ANALYSIS

CROSS-REFERENCES TO RELATED APPLICATIONS

This application is a non-provisional of and claims priority to U.S. Provisional Patent Application No. 62/102,867 entitled "Using Size And Number Aberrations In Plasma DNA For Detecting Cancer" by Lo et al. (attorney docket number 80015-015800US), filed Jan. 13, 2015; and U.S. Provisional Patent Application No. 62/111,524 entitled "Applications Of Plasma Mitochondrial DNA Analysis" by Lo et al. (attorney docket number 80015-016000US), filed Feb. 3, 2015, the disclosure of which is incorporated by reference in its entirety for all purposes.

BACKGROUND

There is much recent interest in the use of cell-free DNA in plasma and serum for molecular diagnostics. For example, mitochondrial DNA has been detected in the plasma (Chiu et al. Clin Chem 2003; 49: 719-726 and Lo et al. Sci Transl Med 2010; 2: 61-ra91). Measurements have been made of mitochondrial DNA in plasma of cancer patients, but such measurements have not been consistent (Yu M et al. Mitochondrial DNA 2012; 23:329-32; Zachariah R R et al. Obstet Gynecol 2008; 112:843-50; Mehra N et al. Clin Cancer Res 2007; 23:421-6; Kohler et al. Mol Cancer 2009; 8: 105; and Choudhuri et al. Mol Cell Biochem 2014; 386: 259-269). Further, the uses of a quantification of the mitochondrial DNA have been limited.

BRIEF SUMMARY

Various embodiments can determine an amount of mitochondrial DNA molecules relative to an amount of nuclear DNA molecules in a biological sample, and use the relative amount for various purposes, e.g., screening, detection, prognostication or monitoring of various physiological and pathological conditions. For example, embodiments show that an amount of mitochondrial DNA can be used to estimate a concentration of DNA of a tissue type.

According to one embodiment, the fetal DNA fraction can be measured by determining an amount of mitochondrial DNA and then mapping the amount to a fetal DNA fraction. Thus, the amount of mitochondrial DNA can be used to estimate a fetal DNA concentration in a sample from a pregnant female, which can reduce costs in such measurements relative to other techniques. The amount of mitochondrial DNA can also be used to estimate a tumor DNA concentration in a sample. And, a percentage of DNA that is from a non-hematopoietic tissue source can be determined.

According to another embodiment, the relative amount of mitochondrial DNA molecules compared to an amount of nuclear DNA molecules in a biological sample can be used to accurately determine a level of cancer for the organism. A random sequencing of DNA molecules can produce sequence reads that are mapped to both a reference nuclear genome and a reference mitochondrial so as to determine whether a DNA molecule is nuclear DNA or mitochondrial DNA. In some implementations, only sequence reads uniquely mapping (aligning) to the mitochondrial genome are used to determine the relative amount. Further, the relative amount of mitochondrial DNA molecules can be used to determine a size of a tumor.

According to another embodiment, the relative amount of mitochondrial DNA molecules compared to an amount of nuclear DNA molecules in a biological sample can be used to accurately determine a level of an auto-immune disease for the organism. Further, a statistical value of a size distribution of mitochondrial DNA molecules can be used to determine a level of an auto-immune disease for the organism, e.g., of systemic lupus erythematosus.

Other embodiments are directed to systems and computer readable media associated with methods described herein.

A better understanding of the nature and advantages of embodiments of the present invention may be gained with reference to the following detailed description and the accompanying drawings.

BRIEF DESCRIPTION OF THE DRAWINGS

FIG. 1 is a table 100 showing tissue type and corresponding number of mitochondria per cell.

TERMS

Figure 2:
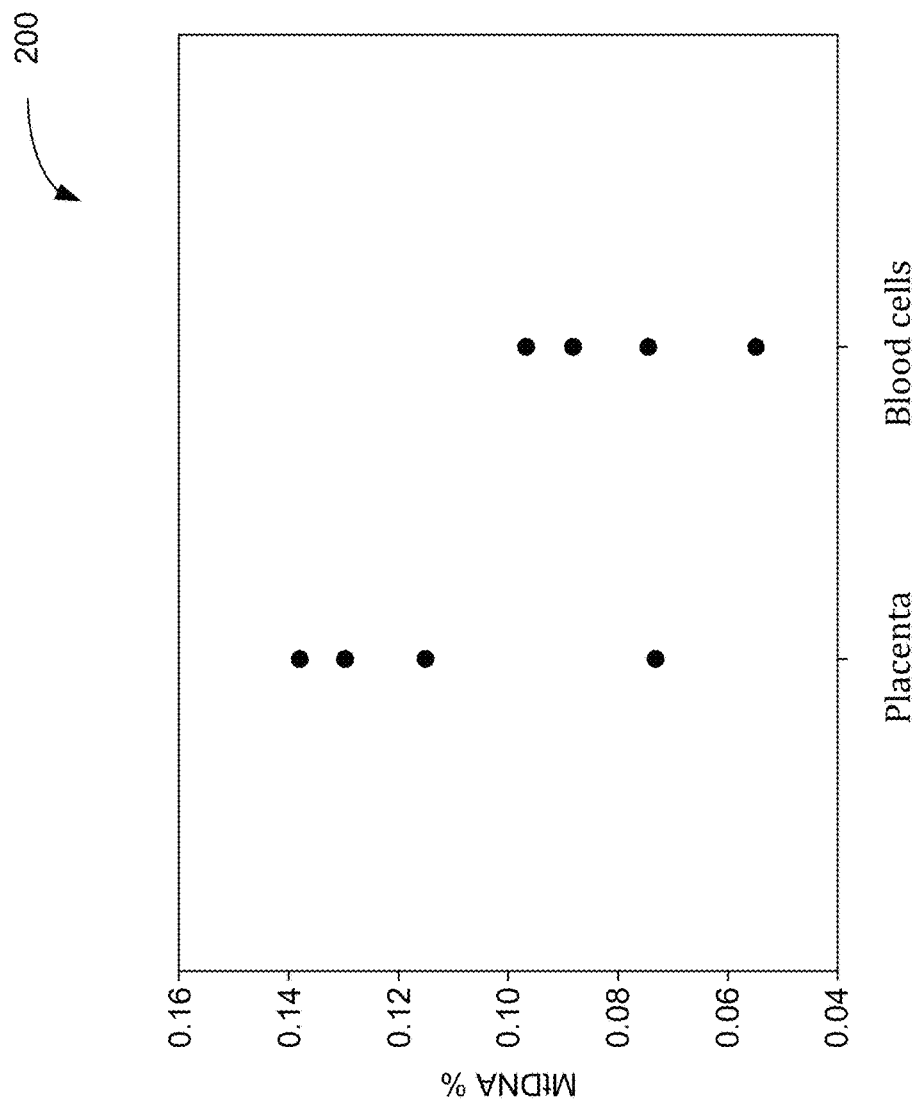
FIG. 2 shows a plot 200 of the fraction of DNA fragments (MtDNA %) aligned to the mitochondrial genome for the placenta and for blood cells according to embodiments of the present invention.

The term "biological sample" as used herein refers to any sample that is taken from a subject (e.g., a human, such as a pregnant woman) and contains one or more nucleic acid molecule(s) of interest. Examples include plasma, saliva, pleural fluid, sweat, ascitic fluid, bile, urine, serum, pancreatic juice, stool, cervical lavage fluid, and cervical smear samples.

The term "nucleic acid" or "polynucleotide" refers to a deoxyribonucleic acid (DNA) and a polymer thereof in either single- or double-stranded form. Unless specifically limited, the term encompasses nucleic acids containing known analogs of natural nucleotides that have similar binding properties as the reference nucleic acid and are metabolized in a manner similar to naturally occurring nucleotides. Unless otherwise indicated, a particular nucleic acid sequence also implicitly encompasses conservatively modified variants thereof (e.g., degenerate codon substitutions), alleles, orthologs, single nucleotide polymorphisms (SNPs), and complementary sequences as well as the sequence explicitly indicated. Specifically, degenerate codon substitutions may be achieved by generating sequences in which the third position of one or more selected (or all) codons is substituted with mixed-base and/or deoxyinosine residues (Batzer M A et al., *Nucleic Acid Res* 1991; 19:5081; Ohtsuka E et al., *J Biol Chem* 1985; 260: 2605-2608; and Rossolini G M et al., *Mol Cell Probes* 1994; 8:91-98).

The term "gene" means the segment of DNA involved in producing a polypeptide chain. It may include regions preceding and following the coding region (leader and trailer) as well as intervening sequences (introns) between individual coding segments (exons).

As used herein, the term "locus" or its plural form "loci" is a location or address of any length of nucleotides (or base pairs) which has a variation across genomes.

The term "sequenced tag" (also called sequence read) refers to a sequence obtained from all or part of a nucleic acid molecule, e.g., a DNA fragment. In one embodiment, just one end of the fragment is sequenced, e.g., about 30 bases. The sequenced tag can then be aligned to a reference genome. Alternatively, both ends of the fragment can be sequenced to generate two sequenced tags, which can provide greater accuracy in the alignment and also provide a length of the fragment. In yet another embodiment, a linear DNA fragment can be circularized, e.g., by ligation, and the part spanning the ligation site can be sequenced.

The term fractional fetal DNA concentration is used interchangeably with the terms fetal DNA proportion and fetal DNA fraction, and refers to the proportion of DNA molecules that are present in a maternal plasma or serum sample that is derived from the fetus and/or the placenta (Lo Y M D et al. *Am J Hum Genet* 1998; 62:768-775; Lun F M F et al. *Clin Chem* 2008; 54:1664-1672).

The term "size profile" generally relates to the sizes of DNA fragments in a biological sample. A size profile may be a histogram that provides a distribution of an amount of DNA fragments at a variety of sizes. Various statistical parameters (also referred to as size parameters or just parameter) can be used to distinguish one size profile to another. One parameter is the percentage of DNA fragment of a particular size or range of sizes relative to all DNA fragments or relative to DNA fragments of another size or range.

The term "parameter" as used herein means a numerical value that characterizes a quantitative data set and/or a numerical relationship between quantitative data sets. For example, a ratio (or function of a ratio) between a first amount of a first nucleic acid sequence and a second amount of a second nucleic acid sequence is a parameter.

The term "classification" as used herein refers to any number(s) or other characters(s) (including words) that are associated with a particular property of a sample. For example, a "+" symbol could signify that a sample is classified as having deletions or amplifications (e.g., duplications). The terms "cutoff" and "threshold" refer to a predetermined number used in an operation. For example, a cutoff size can refer to a size above which fragments are excluded. A threshold value may be a value above or below which a particular classification applies. Either of these terms can be used in either of these contexts.

A "non-hematopoietic tissue source" refers to any organ other than the blood system. Examples include the liver, lung, heart, brain, a non-hematopoietic cancer, the placenta, etc.

The term "nuclear DNA" refers to DNA originating from the nucleus of a cell. A "nuclear genome" corresponds to the nuclear DNA originating from the nucleus of a cell.

The "mitochondrial genome" corresponds to the DNA originating from the mitochondria of a cell.

The term "level of cancer" can refer to whether cancer exists, a stage of a cancer, a size of tumor, how many deletions or amplifications of a chromosomal region are involved (e.g. duplicated or tripled), and/or other measure of a severity of a cancer. The level of cancer could be a number or other characters. The level could be zero. The level of cancer also includes premalignant or precancerous conditions associated with deletions or amplifications.

The term "level of SLE" can refer to whether a patient (or organism) has SLE, the extent of symptoms presented by the patient, or the progress of SLE in particular organs of the patient or overall. The level of SLE can be quantitative (i.e., be represented by a number or fall on a numerical scale) or qualitative. The level of SLE can correlate with or be represented by established metrics of the disease, for example the Systemic Lupus Erythematosus Disease Activity Index (SLEDAI) or the anti-DNA antibody titer in a particular tissue. SLEDAI is an example of a score. The level of SLE can also correspond to the groups into which patients are sorted or triaged, as discussed below (i.e., quiescent, mild activity, and moderate/high activity).

DETAILED DESCRIPTION

Embodiments have identified that a key source of plasma DNA is hematopoietic in origin. Hence, plasma DNA can be viewed as a combination of hematopoietic DNA plus other sources of clinically relevant DNA, e.g. fetal (placental) DNA in the plasma of pregnant women and tumor DNA in the plasma of cancer patients. Results below show that an amount of mitochondrial DNA molecules in a biological sample compared to an amount of nuclear DNA molecules can be used to estimate a fraction of fetal DNA in the sample. Further, a percentage of DNA that is from a non-hematopoietic tissue source can be determined.

In some embodiments, a random sequencing of DNA molecules can provide sequence reads that are used in a mapping procedure to both a reference nuclear genome and a reference mitochondrial genome. Whether a DNA molecule is mitochondrial DNA or nuclear DNA can be determined based on the locations that the sequence reads mapped. A relative amount of mitochondrial DNA in the sample can be determined from the mapped sequence reads. Embodiments can accurately determine a level of cancer using the relative amount, as shown below. Further, the relative amount of mitochondrial DNA can be used to determine the product of the size of the tumor and the amount of mitochondrial DNA within each tumor cell.

Further, per results below, a relative amount of mitochondrial DNA molecules compared to an amount of nuclear DNA molecules in a biological sample can also be used to accurately determine a level an auto-immune disease for the organism. Further, a statistical value of a size distribution of mitochondrial DNA molecules can be used to determine a level an auto-immune disease for the organism, e.g., of systemic lupus erythematosus.

I. Mitochondria in Cells

The number of mitochondria in each cell is widely variable across different tissues, as different cell types can have different number of mitochondria. Mitochondria produce energy and different cells require different amounts of energy. The mitochondria genome is 16 kb.

As a result, the relative abundance of mitochondrial DNA and nuclear DNA in a cell is different in different tissues. Plasma and serum include cell-free mitochondrial DNA and nuclear DNA derived from cells of various tissue in the body. Conditions can exist to change the amount of cell-free DNA derived from certain cells. For example, a pregnancy causes cell-free placental (fetal) DNA to exist in plasma or serum. As another example, a tumor can cause more DNA from the affected tissue to exist in the sample.

The additional cell-free DNA (or new in the case of placenta) from a particular tissue can cause changes in the amount of mitochondrial DNA (MtDNA) in the sample because of the differences in the number of mitochondria in each cell. Accordingly, the quantitative analysis of the absolute and fractional concentrations of mitochondrial DNA in plasma (or serum) can be useful for reflecting the increased or decreased contribution of DNA from a tissue organ resulting from different physiological or pathological conditions.

FIG. 1 is a table 100 showing tissue type and corresponding number of mitochondria per cell. Column 110 lists various tissues. Column 120 lists the number of mitochondrial per cell with an variation. As one could see, the number of mitochondria varies widely. Most of the tissue types have more mitochondria than blood cells, but gastric tissue does have less.

The quantitative analysis of mitochondrial DNA fraction in plasma can be used for the detection of other types of cancers provided that the relative abundance of mitochondrial DNA and nuclear DNA in the cancer tissue is different from (either higher or lower) that of the blood cells. For tissues in which mitochondrial DNA is lower than blood cells, a lower mitochondrial fraction in plasma can be observed. Assuming that each cell contains approximately one set of nuclear DNA, the relative abundance of mitochondrial DNA and nuclear DNA is mainly governed by the number of mitochondria in the cell.

II. Analysis for Fractional Concentration of Fetal DNA in the Plasma of Pregnant Women Fetally-derived DNA is present in the cell-free plasma of pregnant women (Lo et al. Lancet 1997; 350:485-7). The fractional concentration of fetal DNA (also called fetal DNA fraction (F %)) in a maternal plasma sample is an important parameter governing the accuracies of various noninvasive prenatal tests based on the analysis of maternal plasma DNA, for example, in the noninvasive prenatal testing for chromosomal aneuploidies (Chiu et al. BMJ 2011; 342: c7401). Some embodiments provide methods for determining the fractional concentration of fetal DNA in a maternal plasma sample through the quantitative analysis of mitochondrial DNA in a maternal sample. Although example results are provided for plasma, embodiments may be used with other samples (e.g., serum or urine) that includes mitochondrial DNA fragments.

A. Plasma MtDNA % for Different Tissue

In healthy subjects, cells in the hematopoietic system are the main source of circulating cell-free DNA in plasma (Lui et al. Clin Chem 2002; 48: 421-427). In a pregnant woman, the placenta releases DNA into the maternal circulation. The placentally-derived DNA carries the genetic information of the fetus and is commonly referred to as 'fetal DNA' in the field of noninvasive prenatal testing. Thus, fetal DNA encompasses placentally-derived DNA and any other DNA derived from the fetus. An analysis of the mitochondrial and nuclear DNA in the placenta and blood cells was performed as a check of measurement techniques and correspondence to the data in table 100.

To determine the relative abundance of mitochondrial and nuclear DNA in the placenta and blood cells, we sequenced placental tissues and corresponding blood cells samples of four pregnant women using the Illumina HiSeq series of sequencers. Genomic DNA was extracted from buffy coat samples according to the blood and body fluid protocol of the QIAamp DSP DNA Blood Mini Kit. DNA was extracted from placental tissues with the QIAamp DNA Mini Kit (Qiagen). Five micrograms of genomic DNA was sheared with a Covaris S220 Focused-ultrasonicator to approximately 200 bp. Sequencing libraries of the DNA samples were then constructed with the Paired-End Sample Preparation Kit (Illumina). The sequencing library of each sample was sequenced using the Illumina HiSeq series of sequencers. Seventy-five nucleotides were sequenced from each of the two ends of a DNA fragment. The paired-end sequencing data were analyzed by means of the Short Oligonucleotide Alignment Program 2 (SOAP2) (Li et al. Bioinformatics 2009; 25:1966-7) in the paired-end mode. For each paired-end read, 75 by from each end were aligned to a reference sequence comprising of both the non-repeat-masked reference human nuclear genome (hg19) and the human mitochondrial genome. Up to 2 nucleotide mismatches were allowed for the alignment of each end. Reads that were mapped to a unique position of the combined human nuclear and mitochondrial genome were used for down-stream analysis. The fraction (proportion) of DNA fragments that were aligned to the mitochondrial genome (denoted as MtDNA %) was determined for each sample.

FIG. 2 shows a plot 200 of the fraction of DNA fragments (MtDNA %) aligned to the mitochondrial genome for the placenta and for blood cells according to embodiments of the present invention. Each data point corresponds to a percentage of the DNA that is mitochondrial DNA (MtDNA %) in a particular tissue sample of the placenta or red blood cells. As is expected from table 100, the placenta tissue samples generally have a higher MtDNA %.

Because of the higher mitochondrial DNA fraction in the placenta, the fractional concentration of placentally-derived fetal DNA would affect the concentration (absolute or fractional) of mitochondrial DNA in the plasma of pregnant women. A higher fetal DNA fraction is expected to be associated with a higher concentration of mitochondrial DNA in the maternal plasma. The absolute concentration of mitochondrial DNA still relies on a known concentration of DNA in a sample, and thus still has a factional/percentage aspect. For example, an amount of DNA in a plasma sample is known to have a specific DNA concentration. Thus, assuming that a new sample has the known concentration, the absolute concentration of mitochondrial DNA can be used.

Figure 3:
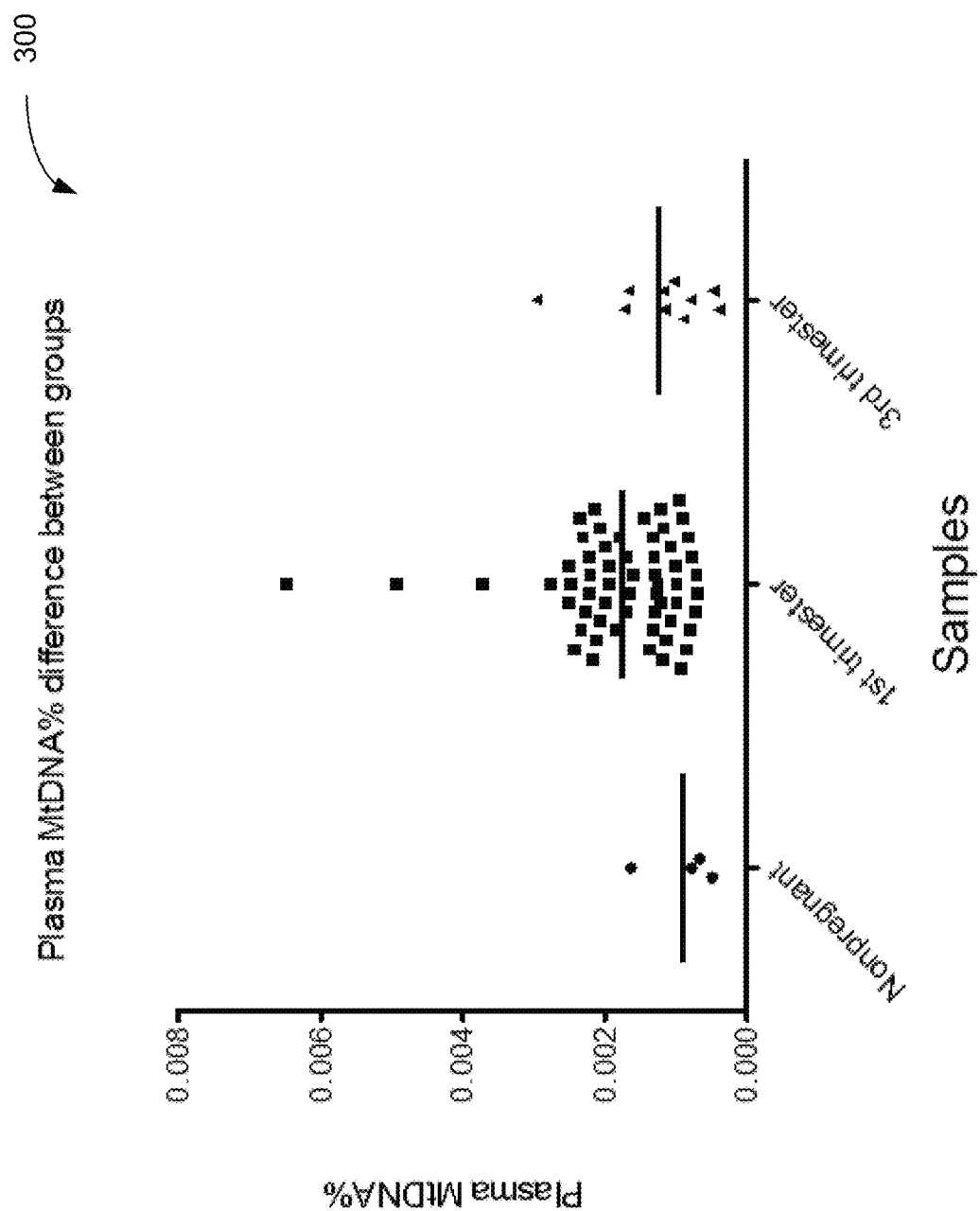
FIG. 3 shows a plot 300 of plasma MtDNA % for non-pregnant and pregnant samples ($1^{st}$ trimester and $3^{rd}$ trimester) according to embodiments of the present invention.

FIG. 3 shows a plot 300 of plasma MtDNA % for non-pregnant and pregnant samples ($1^{St}$ trimester and $3^{rd}$ trimester) according to embodiments of the present invention. DNA fragments from four non-pregnant female plasma samples, 59 1st trimester pregnancy plasma samples, and 10 3rd trimester pregnancy plasma samples were sequenced. The mean plasma MtDNA % for non-pregnant female was 0.0009%; 1st trimester was 0.0017%; and 3rd trimester was 0.0012%. The 1st trimester samples are significantly higher than those from non-pregnant women (Mann Whitney test, p-value=0.017) and 3rd trimester samples (Mann Whitney test, p-value=0.054). Thus, it can be seen that the proportions of MtDNA in plasma samples in pregnant cases are higher than non-pregnant female individuals.

Figure 4:
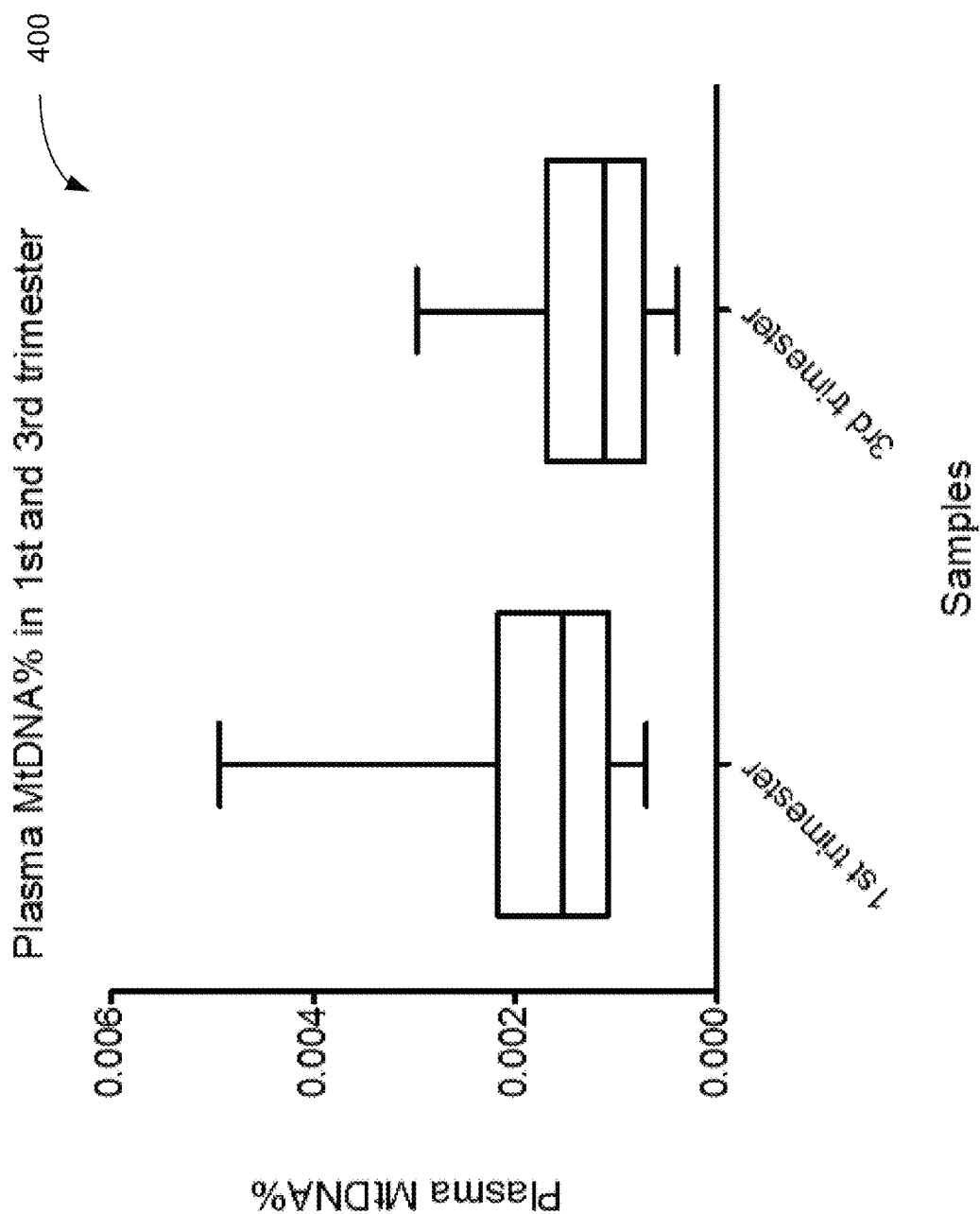
FIG. 4 shows a plot 400 of plasma MtDNA % difference between $1^{st}$ trimester and $3^{rd}$ trimester pregnancy according to embodiments of the present invention.

FIG. 4 shows a plot 400 of plasma MtDNA % difference between $1^{st}$ trimester and $3^{rd}$ trimester pregnancy according to embodiments of the present invention. The 1st trimester pregnancy has a higher plasma mitochondrial DNA % than non-pregnant (see FIG. 3) and 3rd trimester pregnancy samples. The mitochondrial DNA content is typically higher in the $1^{st}$ trimester placental cells than in the $3^{rd}$ trimester placental cells (see FIG. 5), thereby leading to the higher measurements for the $1^{st}$ trimester samples.

Figure 5:
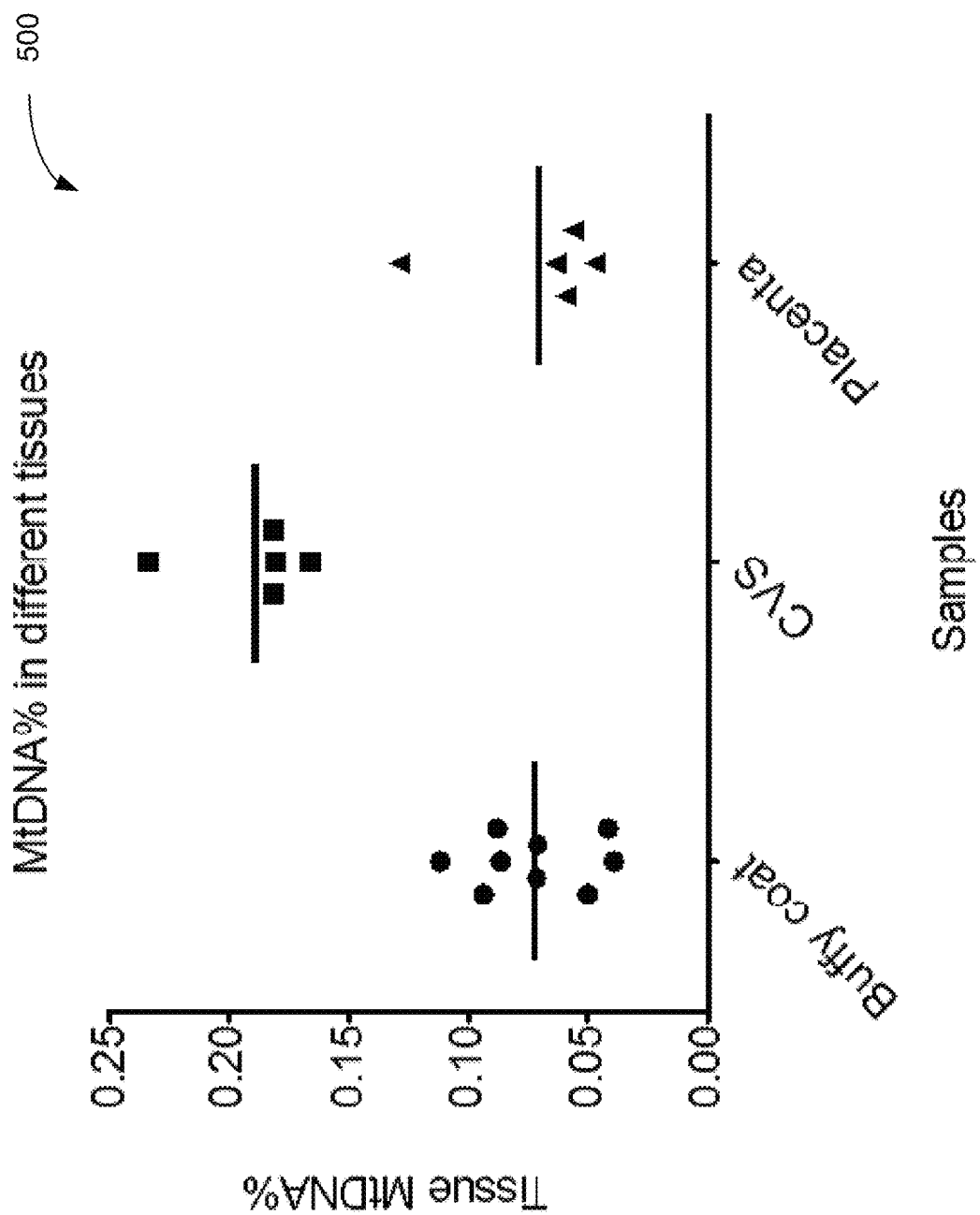
FIG. 5 shows a plot 500 of mitochondrial DNA percentage (MtDNA %) in buffy coat (BC), chorionic villus sampling (CVS), and placenta ($3^{rd}$ trimester) according to embodiments of the present invention.

FIG. 5 shows a plot 500 of mitochondrial DNA percentage (MtDNA %) in buffy coat (BC), chorionic villus sampling (CVS), and placenta ($3^{rd}$ trimester) according to embodiments of the present invention. The CVS is taken in the 1st trimester. The MtDNA % in buffy coat, CVS, and placenta was measured and compared. The mean MtDNA % of buffy coat, CVS, and placenta are: 0.073%, 0.189% and 0.07% respectively. CVS has a significantly higher MtDNA % than both buffy coat (Mann Whitney test, =0.001) and placenta (T-test, p-value=0.008) while the placenta has no significant difference with buffy coat. The placenta was measured for the third trimester. Thus, the differences in the plasma MtDNA % can be explained by the tissue MtDNA %.

The above data indicates that the amount of MtDNA in a sample relates to the fetal DNA concentration, especially before the third trimester, as the MtDNA is higher for samples that are known to have higher fetal DNA concentrations. The following section provides more specific data that shows that MtDNA % is proportional to fetal DNA concentration.

B. MtDNA % Proportional to F %

Since placental cells have more mitochondria per cell and placenta is the predominant contributor of fetal DNA in maternal plasma, the contribution to a plasma sample is higher when there is fetal DNA in the plasma sample. Further, there would be a higher proportion of MtDNA when the fetal DNA concentration is higher. The following proves this relationship to be true.

Figure 6:
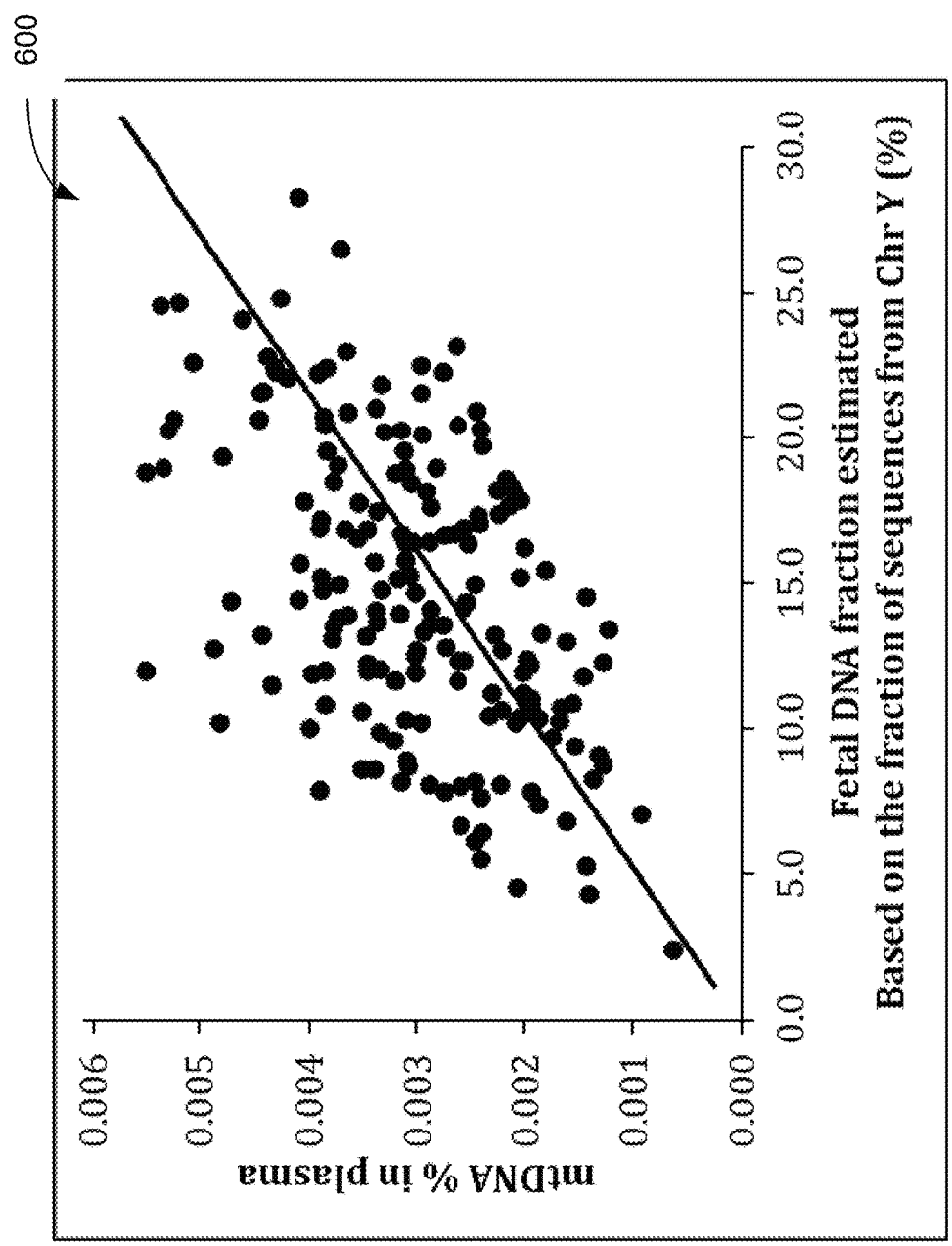
FIG. 6 is a plot 600 showing a positive correlation between the mitochondrial DNA fraction and the fetal DNA fraction in plasma samples according to embodiments of the present invention.

FIG. 6 is a plot 600 showing a positive correlation between the mitochondrial DNA fraction and the fetal DNA fraction in plasma samples according to embodiments of the present invention. Each data point corresponds to a different plasma sample. The vertical axis shows the MtDNA % in the plasma sample. The horizontal axis shows the fetal DNA fraction (concentration). For this data, the fetal DNA fraction is determined using chromosome Y from male fetuses. The positive correlation is R=0.51 (Pearson correlation) with confidence of P<0.001. Accordingly, one can see that MtDNA % can be used to estimate the fetal DNA fraction. Other techniques can be used to determine the fetal DNA fraction. Another example is the use of paternally-inherited genetic markers such as single nucleotide polymorphisms or simple tandem repeat polymorphisms or insertion-deletion polymorphisms. Another example is the use of epigenetic markers such as regions that are differentially methylated between fetal and maternal DNA (Poon et al. Clin Chem 2002; 48: 35-41; Chiu et al. Am J Pathol 2007; 170: 941-950; Chan et al. Clin Chem 2006: 52: 2211-2218; U.S. Pat. No. 6,927,028). The above markers can be analyzed using methods known to those of skill in the art, including polymerase chain reaction (PCR), digital PCR, sequencing, massively parallel sequencing and targeted massively parallel sequencing.

To obtain the data for FIG. 6, plasma samples of 182 pregnant women each carrying a male fetus were sequenced using the Illumina HiSeq 2500 system. For each pregnant woman, DNA extracted from 2.5 mL to 4 mL plasma was used for constructing the sequencing library using the TruSeq DNA Sample Prep Kit (Illumina, Inc). The sequencing was performed in a 12-plex format. In other words, bar-coded sequencing libraries of 12 samples were loaded onto one lane of an Illumina flow cell for sequencing. After the sequencing, the sequenced reads for each sample were identified by the sample-specific barcode. A single end protocol was used for the sequencing. Thirty-six nucleotides were sequenced for each sequenced DNA fragment. The sequencing data were aligned to a reference sequence comprising both the non-repeat-masked reference human nuclear genome (hg19) and the human mitochondrial genome using the SOAP2 program. Reads that were mapped to a unique position of either the human nuclear or mitochondrial genome were used for down-stream analysis. The fraction of DNA fragments that were aligned to the mitochondrial genome (denoted by MtDNA %) was calculated for each sample. The fetal DNA fraction was determined based on the fraction of DNA fragments aligning to the Y chromosome as previously described (Chiu et al. BMJ 2011; 342: c7401). As there is considerable homology between the mitochondrial genome and the nuclear genome, all sequenced reads that were initially mapped to the mitochondrial genome were further realigned to a combined nuclear and mitochondrial genome using a more stringent requirement of mapping accuracy.

The data from FIG. 3 also shows a correlation between the plasma MtDNA % and the fetal DNA concentration F %. In some embodiments, the fetal DNA fraction (F %) calculation from the proportion of chromosome Y sequences can be performed as follows. For cases of pregnancy with a male fetus, fetal DNA fraction (F %) can be deduced from proportion of reads aligned to chromosome Y (ChrY %). A very small proportion of sequenced reads from pregnant women carrying a female fetus would be aligned wrongly on chromosome Y (Chiu et al., 2008). Hence, the ChrY % from the plasma of pregnancy of a male fetus is composed of the misaligned reads and the true reads derived from the male fetus. To deduce the F %, the following equation can be used:

$$\text{ChrY \%} = [\text{ChrY \%}_{male} \times F \%] - [\text{ChrY \%}_{female} \times (1-F \%)]$$

ChrY $\%_{male}$ is the proportion of reads aligned on chromosome Y in a plasma sample containing 100% male DNA while ChrY %–female is the proportion of reads aligned on chromosome Y in a plasma containing 100% female DNA (misaligned reads). ChrY $\%_{male}$ and ChrY $\%_{female}$ can be determined from control samples.

Figure 7:
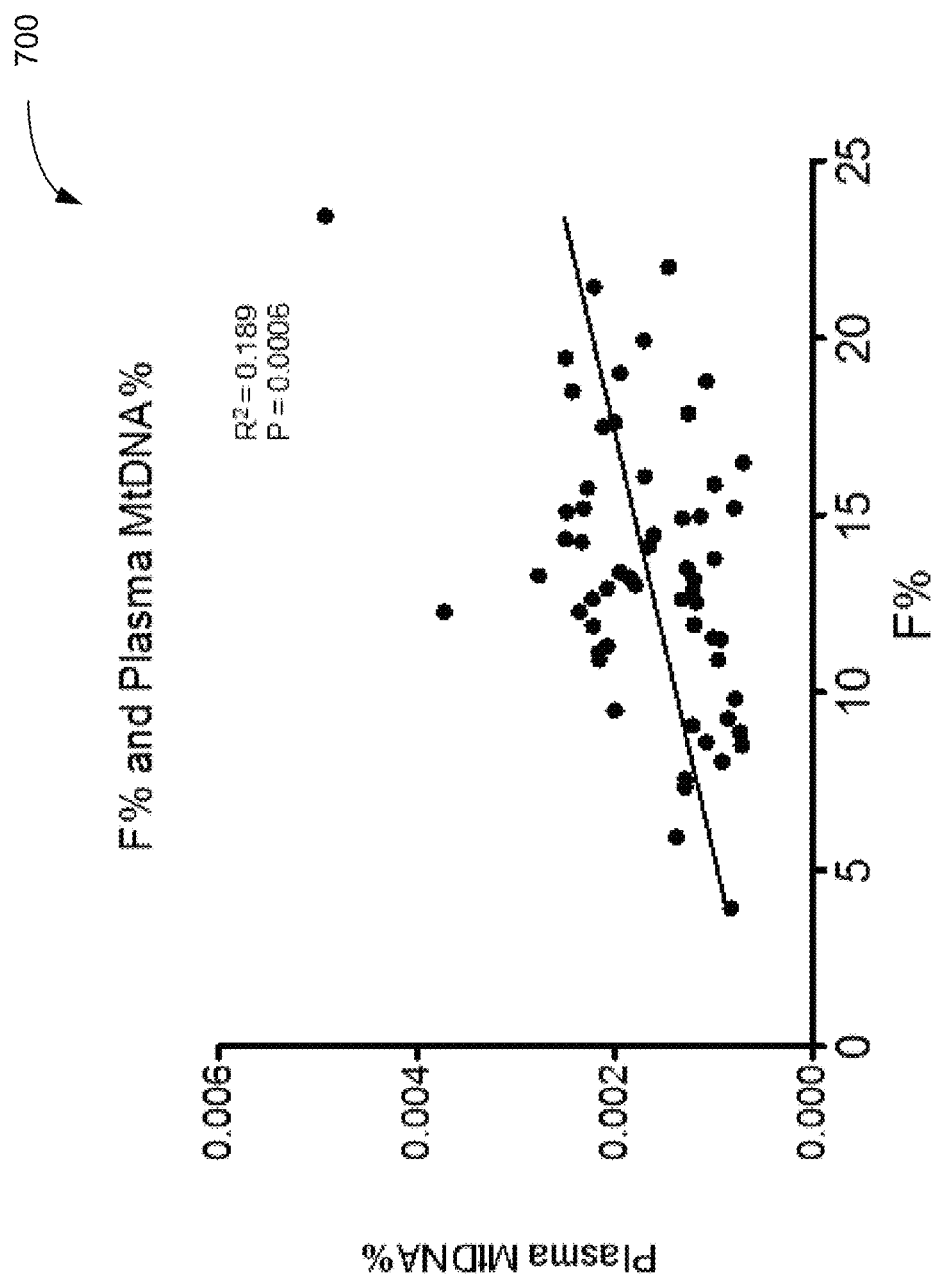
FIG. 7 is a plot 700 showing a correlation between fetal DNA fraction and plasma mitochondrial DNA percentage in 1st trimester pregnancy according to embodiments of the present invention.

FIG. 7 is a plot 700 showing a correlation between fetal DNA fraction and plasma mitochondrial DNA percentage in 1st trimester pregnancy according to embodiments of the present invention. F % and plasma MtDNA % were measured from the 59 1st trimester plasma samples from FIG. 3. There is a positive correlation between plasma MtDNA % and F % of the sample (p-value=0.0006; $R^2$=0.189. Accordingly, it has been shown that MtDNA % consistently correlates with the factional fetal concentration F %.

C. Quantification of F % Using MtDNA %

Because of the correlation between the fetal DNA fraction and mitochondrial DNA fraction in plasma, the quantification of plasma mitochondrial DNA fraction can be used for measuring the fetal DNA fraction in the maternal plasma sample. Thus, MtDNA % can be used to determine the fetal DNA fraction. A benefit is that the MtDNA % can be computed without having to differentiate fetal DNA from maternal DNA. And, single end sequencing can be used, as opposed to paired-end sequencing, as would be used if size of DNA fragments was used to determine the fetal DNA concentration. Thus, the sequencing cost can be reduced by using single end sequencing.

To test the ability to predict the fetal DNA concentration, we randomly divided all the 182 plasma samples used for FIG. 6 into two sets, namely a training set and a validation set. The training set was used to determine the relationship of the plasma mitochondrial DNA fraction and the fetal DNA fraction. Then, in the validation set, the mitochondrial DNA fraction was used to deduce the fetal DNA fraction based on the formula determined from the training set.

Figure 8:
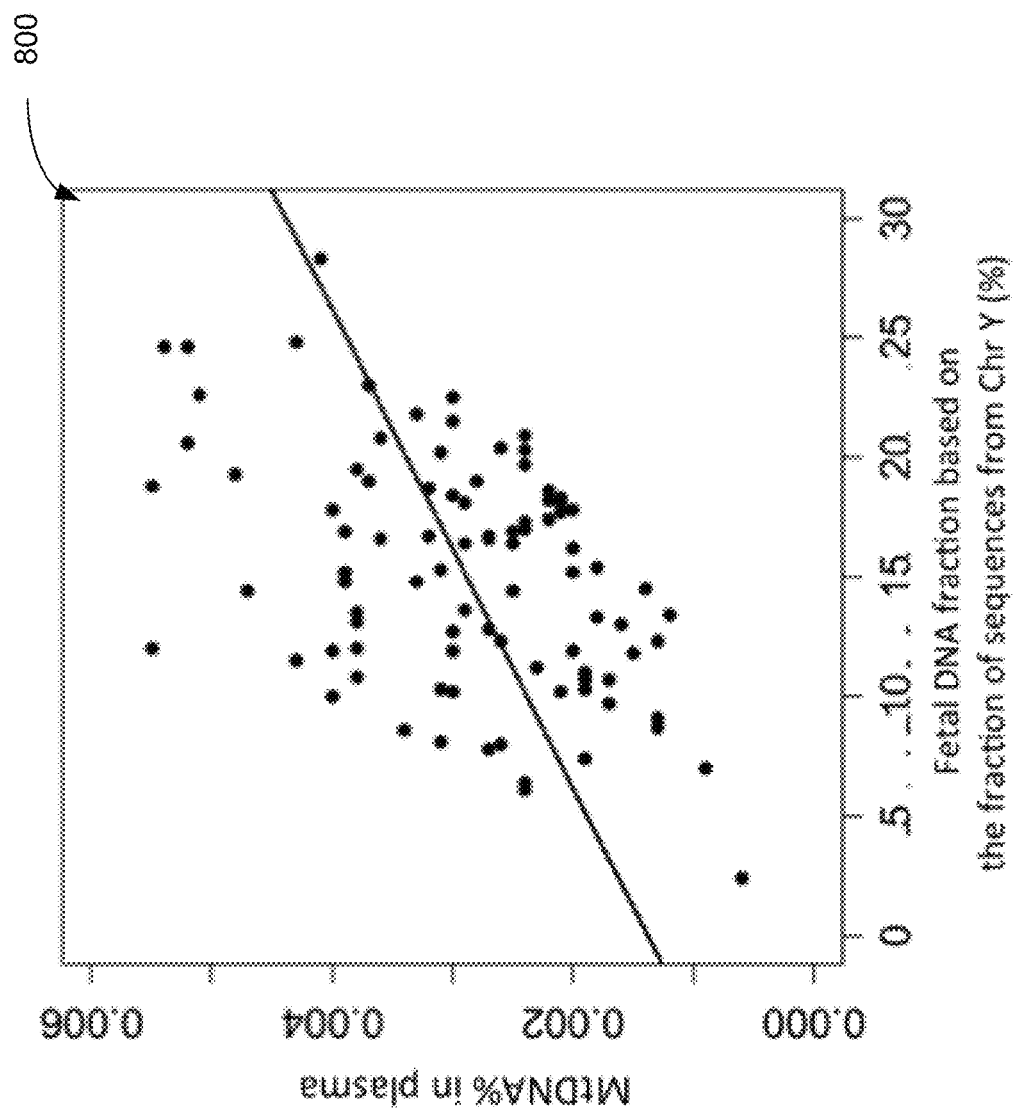
FIG. 8 shows a plot 800 of training data for determining a functional relationship between the mitochondrial DNA fraction and the fetal DNA fraction in plasma according to embodiments of the present invention.

FIG. 8 shows a plot 800 of training data for determining a functional relationship between the mitochondrial DNA fraction and the fetal DNA fraction in plasma according to embodiments of the present invention. For the training set, the relationship (calibration function) between the mitochondrial DNA fraction and fetal DNA fraction was determined as $$\text{MtDNA \%} = F\% \times 0.0001226335 + 0.001141848\%$$

where MtDNA is the mitochondrial DNA fraction (in %) in the plasma sample; and F is the fetal DNA fraction (in %) of the sample. For the validation set, the mitochondrial DNA fraction of each sample was used to deduce the fetal DNA fraction in the sample according to the formula.

Figure 9:
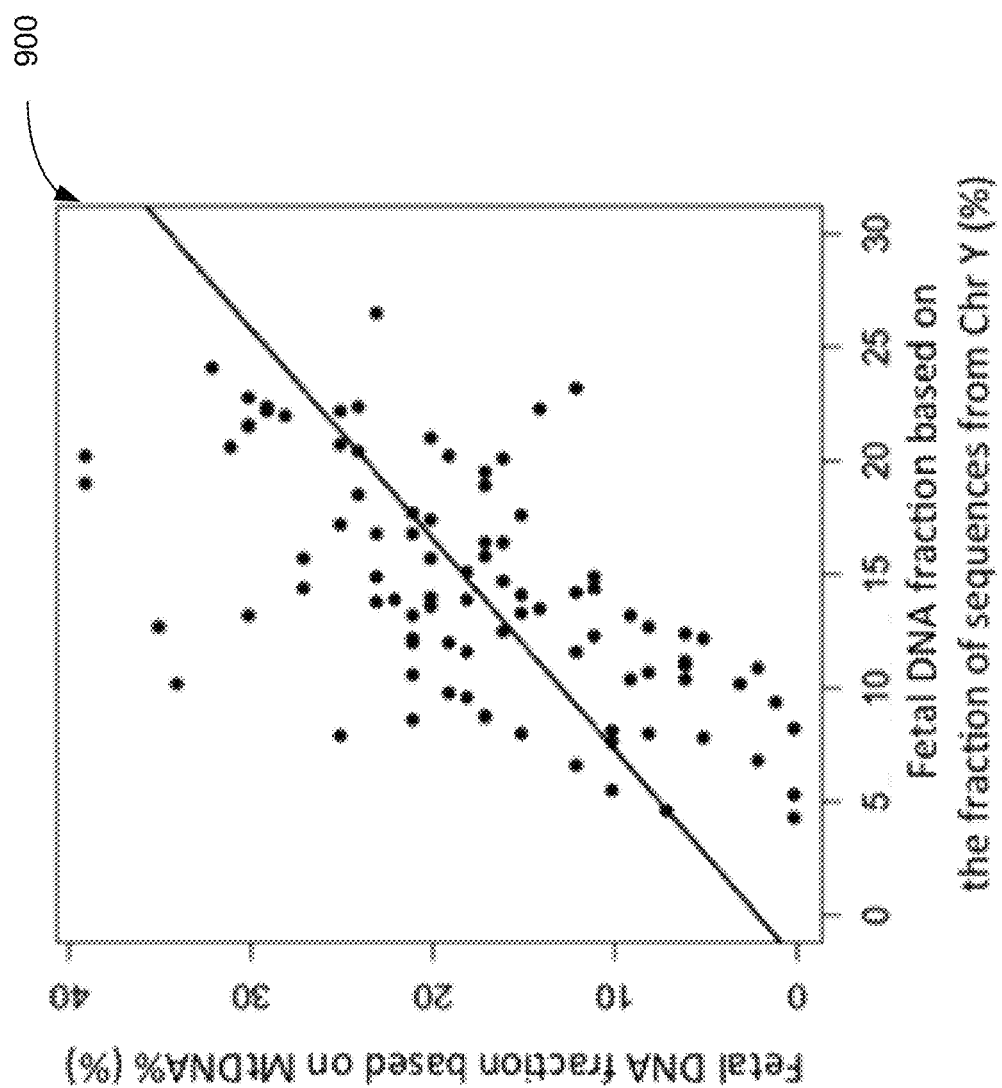
FIG. 9 shows a plot 900 of fetal DNA fraction deduced from the mitochondrial DNA fraction plotted against the measured fetal DNA fraction based on the fraction of plasma DNA fragments aligned to the Y chromosome according to embodiments of the present invention.

FIG. 9 shows a plot 900 of fetal DNA fraction deduced from the mitochondrial DNA fraction plotted against the measured fetal DNA fraction based on the fraction of plasma DNA fragments aligned to the Y chromosome according to embodiments of the present invention. The deduced and measured fetal DNA fraction showed a good correlation (R=0.61, P<0.001, Pearson correlation). The median deviation of the deduced value from the measured value was 5.1% (interquartile range: 2.6% to 8.2%).

Accordingly, a calibration function can be determined that provides a relationship between a MtDNA concentration and a fetal DNA concentration for a sample. When a new sample is obtained from a new subject, the MtDNA concentration can be measured, and the a calibration function can be used to convert the MtDNA concentration into the fetal DNA concentration. The MtDNA concentration can be a fractional concentration or a relative concentration, although an absolute concentration would still assume some fractional representation based on typical DNA concentrations. As examples, absolute concentration can be expressed as an amount per volume (e.g., assuming a particular concentration of total DNA per mL) or per ng DNA, both of which involve some measure of nuclear DNA.

In various embodiments, a concentration of the mitochondrial DNA in plasma can be measured by, for example but not limited to, real-time PCR (Chiu et al. Clin Chem 2003; 49: 719-726), digital PCR (Lo et al. Proc Natl Acad Sci USA 2007; 104: 13116-13121) and mass spectrometry (Ding et al. Proc Natl Acad Sci USA 2004; 101: 10762-10767). For example, primers and probes for both MtDNA and nuclear (nDNA) can be used to measure respective amounts, and a ratio can be taken. As another example, primers can target the homologous regions in the nuclear and mitochondrial genome, and probes or mass spectrometry can be used to distinguish the two, so as to get the respective amounts. As a further example, primers and probes that only measure the mitochondrial DNA can be used to determine an amount of MtDNA, where the amount can be expressed in relation to the amount of total DNA (majority being nuclear DNA) added to the reaction (e.g., measured by spectrophotometry) or the volume of sample added to the reaction. There are typically ranges of total DNA (majority being nuclear DNA) contained within each milliliter of maternal plasma. Accordingly, a total amount of DNA (e.g., per volume or mass) can be used to obtain the MtDNA concentration. In other embodiments, measurements of the absolute concentrations of mitochondrial DNA and the nuclear DNA can be done separately and then combined to obtain a relative amount of MtDNA to nuclear DNA. The fetal DNA concentration can then be deduced based on the two concentrations, for example, but not limited to the ratio or the difference of these two values.

Further evidence of MtDNA % being correlated to the fetal DNA fraction can be seen by the correlation of the MtDNA % being correlated to the size of nuclear DNA fragments. A correlation between the size of nuclear DNA fragments and fetal DNA fraction has been previously shown in U.S. Patent Publication 2013/023743, which is incorporated by reference in its entirety.

Figure 10:
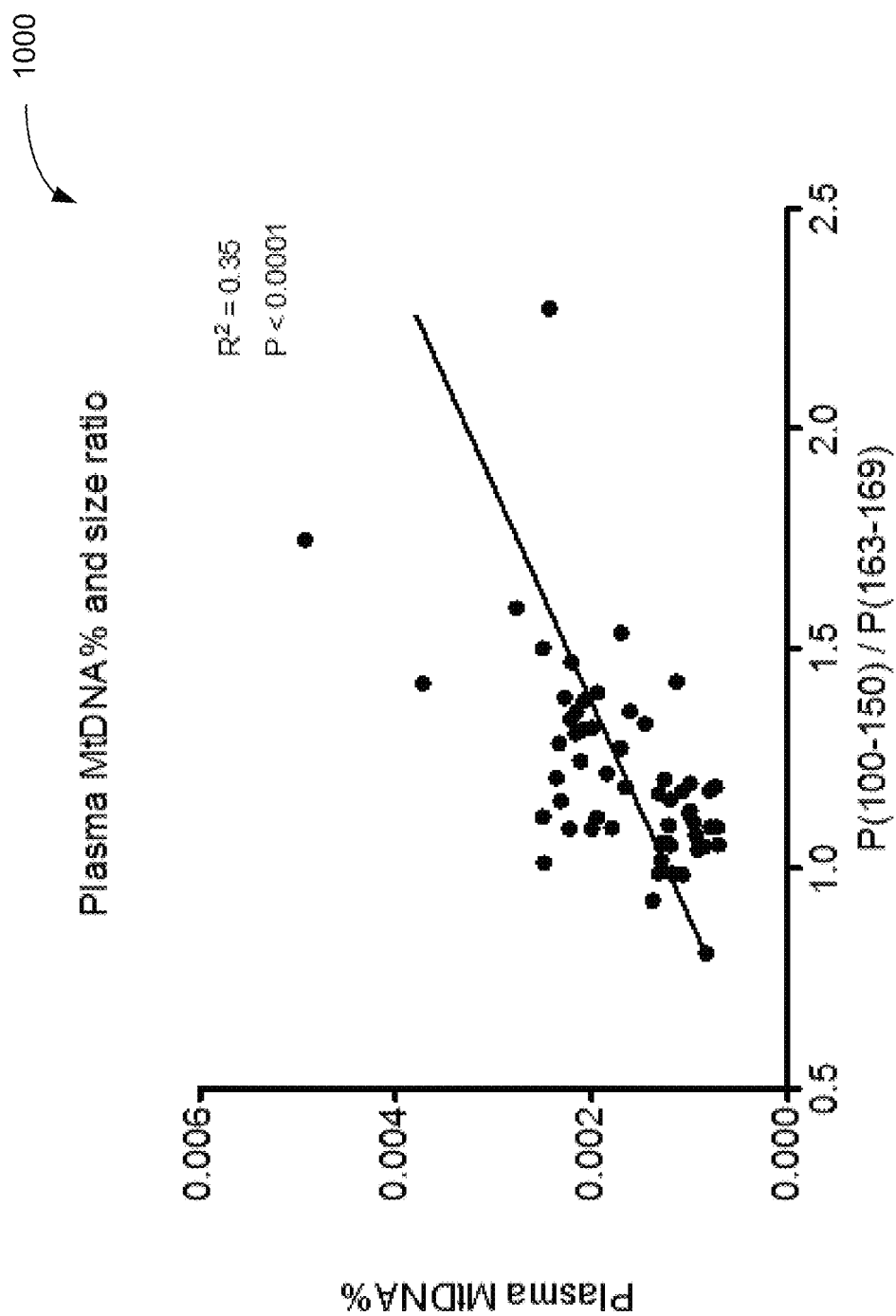
FIG. 10 is a plot 1000 showing a correlation between a plasma DNA size ratio and plasma MtDNA % of 1st trimester samples according to embodiments of the present invention.

FIG. 10 is a plot 1000 showing a correlation between a plasma DNA size ratio and plasma MtDNA % of 1st trimester samples according to embodiments of the present invention. The 59 1st trimester plasma samples from FIG. 3 were used. Plasma MtDNA % were found to be significantly correlated with the size ratio (p-value<0.0001, $R^2$=0.35). In this example, the plasma DNA size profile was determined as:

$$\text{Size Ratio} = \frac{P(100-150)}{P(163-169)}.$$

P(100-150) is the proportion of nuclear DNA fragments of mother and fetus between 100 by and 150 by in length. P(163-169) is the proportion of DNA fragments between 163 by and 169 by in length.

A disadvantage of using such a size ration to determine the fetal DNA concentration is that one has to do paired-end sequencing. On the other hand, one can obtain MtDNA % even with single-end sequencing without the extra sequencing costs of sequencing both ends.

D. Method

As described above, embodiments can determine an amount of the plurality of DNA molecules that are mitochondrial DNA in the biological sample and estimate a fetal DNA concentration in the sample based on the determined amount. The amount may be the proportion of the plurality of DNA molecules that are mitochondrial DNA in the biological sample. In other embodiments, the amount may be a concentration of MtDNA, e.g., per unit volume, such as mL. In one embodiment, real-time PCR can be used to determine an absolute concentration of MtDNA and determine the fetal DNA concentration using a similar functional approximation as shown for MtDNA percentage.

Figure 11:
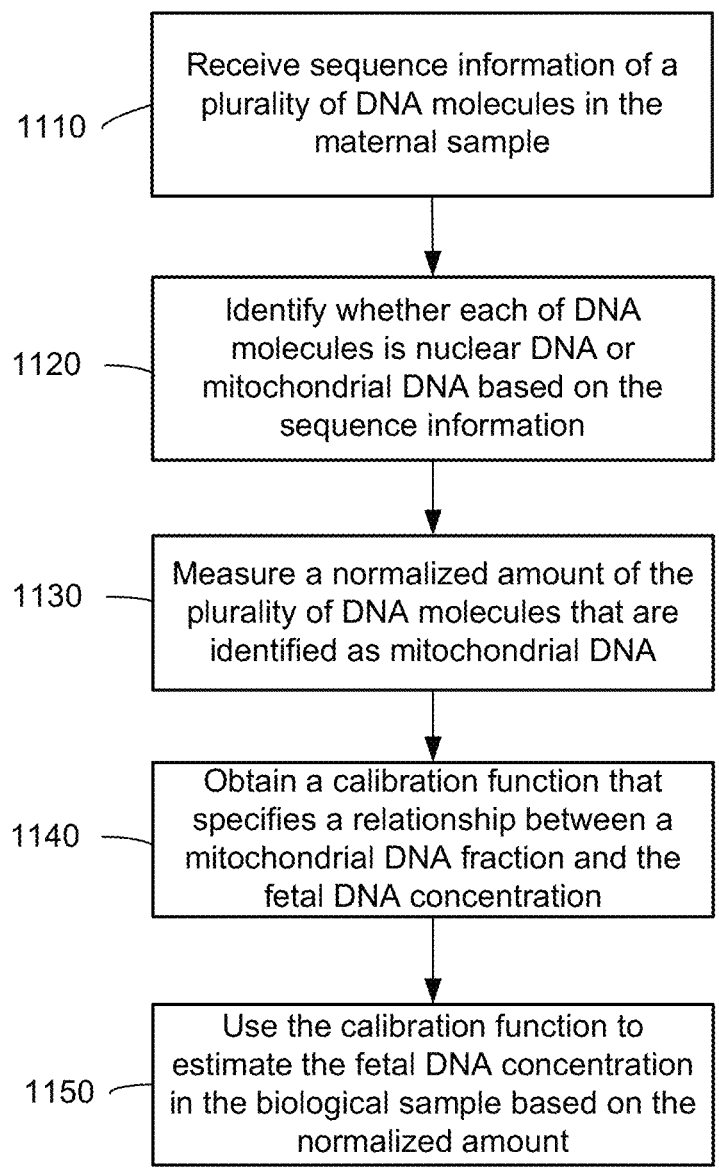
FIG. 11 is a flowchart illustrating a method 1100 of analyzing a biological sample of a female subject pregnant with a fetus to estimate a fetal DNA concentration in the biological sample according to embodiments of the present invention.

FIG. 11 is a flowchart illustrating a method 1100 of analyzing a biological sample of a female subject pregnant with a fetus to estimate a fetal DNA concentration in the biological sample according to embodiments of the present invention. In some embodiments, the biological sample can be plasma or serum. The biological sample includes cell-free DNA from the female subject and the fetus. The cell-free DNA of the biological sample include mitochondrial DNA and nuclear DNA.

In one implementation, the biological sample may be received at a machine, e.g., a sequencing machine, which outputs measurement data (e.g., sequence reads) that can be used to determine whether the DNA fragments are nuclear DNA or mitochondrial DNA. Method 1100 may be performed wholly or partially with a computer system, as can other methods described herein.

At block 1110, sequence information of a plurality of DNA molecules in the biological sample is received at a computer system. As an example, the number of DNA molecules for which sequence information is obtained can be at least 500,000. This number of DNA molecules can be analyzed for other methods described herein.

The sequence information can be obtained in a variety of ways. For example, the sequence of a DNA molecule can be received as a single measurement of a particular color of a probe that corresponds to a particular sequence. In other embodiments, the sequence of a DNA molecule can be determined from sequencing measurements for each base, e.g., an intensity signal for each base. In one implementation, DNA molecules are randomly sequenced using adaptors.

At block 1120, for each of a plurality of DNA molecules in the biological sample, it is determined whether the DNA molecule is a nuclear DNA molecule or a mitochondrial DNA molecule. The location of the DNA molecule can be determined in a reference nuclear genome or a reference mitochondrial genome using the sequence information for the DNA molecule. If the DNA molecule is determined to be located in the reference nuclear genome, then the DNA molecule is identified as nuclear DNA. If the DNA molecule is determined to be located in the reference mitochondrial genome, then the DNA molecule is identified as mitochondrial DNA. If the DNA molecule is not determined to be located only in the reference nuclear genome or the reference mitochondrial genome with sufficient accuracy, then the DNA molecule can be discarded, and thus would not be included in the plurality of DNA molecules analyzed.

As part of determining a location of a DNA fragment (molecule), the DNA fragments can be sequenced to obtain sequence reads, and the sequence reads can be mapped (aligned) to the reference nuclear genome or reference mitochondrial genome. If the organism was a human, then the reference genomes would be reference human genomes, potentially from a particular subpopulation. As another example, the cell-free DNA fragments can be analyzed with different probes (e.g., following PCR or other amplification), where each probe corresponds to a different location. In some embodiments, the analysis of the cell-free DNA fragments can be performed by receiving sequence reads or other experimental data corresponding to the cell-free DNA fragments, and then analyzing the experimental data using a computer system.

At block 1130, a normalized amount of the plurality of DNA molecules that are identified as mitochondrial DNA is measured. An amount of mitochondrial DNA can be determined in various ways. For example, the number of mitochondrial DNA fragments can be counted. As another example, a number of bases of the mitochondrial DNA fragments can be counted.

The amount can be normalized in a variety of ways. For example, the total usable DNA molecules (i.e., ones for which an identification has been made) can be used to normalize by dividing the amount of mitochondrial DNA molecules. A same result occurs when the same number of usable DNA molecules are always used. Another example is a ratio of the amount of mitochondrial DNA molecules and an amount of nuclear DNA molecules. Accordingly, the normalized amount can be relative to a second amount of the plurality of DNA molecules including DNA molecules that are identified as nuclear DNA molecules. As examples, the second amount could be of nuclear and mitochondrial DNA molecules or just the nuclear DNA molecules. A ratio of the first amount and the second amount can be computed to obtain the normalized amount.

In one embodiment, the normalized amount is a plasma mitochondrial DNA percentage. The plasma mitochondrial DNA percentage (Plasma MtDNA %) calculation can be performed as follows. The plasma mitochondrial DNA percentage (Plasma MtDNA %) can correspond to the proportion of reads mapped uniquely on mitochondrial DNA genome. It reflects the mitochondrial DNA contribution in plasma, and can be calculated as following:

$$\text{Plasma } MtDNA \% = \frac{\text{Number of reads uniquely mapped on mitochondrial genome}}{\text{Total usable aligned reads}} \times 100\%.$$

Accordingly, in one embodiment, the normalized amount of the plurality of DNA molecules corresponds to a proportion of mitochondrial DNA in the biological sample. A first amount of the plurality of DNA molecules that are mitochondrial DNA can determined, and a second amount of the DNA molecules that are identified as being nuclear DNA can be determined. A ratio (e.g., the percentage shown above) of the first amount and the second amount can be computed as part of determining the normalized, e.g., multiplicative factors can be applied, such as the 100% scaling.

In other embodiments, the normalized amount may be a concentration of MtDNA, e.g., per unit volume, such as mL, or per mass/weight of DNA. In embodiments where determining the locations of the plurality of DNA molecules is made only for the reference mitochondrial genome (e.g., using MtDNA specific probes), all of the plurality of DNA molecules whose location is determined would be mitochondrial DNA. In such embodiments, a first amount of the plurality of DNA molecules that are identified as mitochondrial DNA is measured, e.g., using the probes. And, a total amount of DNA in the biological sample (the total amount of DNA including nuclear DNA) can be measured, e.g., as described above. The normalized amount would use a ratio of the first amount and the total amount to obtain the relative amount of MtDNA to a second amount (e.g., the total amount) of the plurality of DNA molecules including DNA molecules that are identified as nuclear DNA molecules.

At block 1140, a calibration function that specifies a relationship between a mitochondrial DNA concentration and the fetal DNA concentration is obtained. An example of a calibration function is the function from above: MtDNA %=F %×0.0001226335+0.001141848%. This function provides a value for MtDNA % for each value of F %. Rearranging this function provides a value of F % for each value of MtDNA %:

$$F \% = \frac{MtDNA \% - 0.001141848\%}{0.0001226335}.$$

Such a calibration function can be obtained by reading 0.0001226335 and 0.001141848 (examples of the coefficients) from memory.

The calibration function be defined in a variety of ways, e.g., as a plurality of coefficients of a specified function, such as a linear or non-linear function. Other embodiments can store a plurality of calibration data points (e.g., data points of the calibration function) so that the calibration function can be generated. Further, an interpolation can be performed between such calibration data points to obtain the calibration function. Regardless of how the calibration function is defined, the values can be retrieved from memory.

The calibration data points and thus the calibration function can be determined from calibration samples, as described above. Examples of such calibration samples include the data used for FIG. 6 and FIG. 7. In these samples, the fetal DNA fraction was known, and thus these samples can be considered calibration samples. The normalized amount can be measured for each of these samples for which the fetal DNA fraction is known. A calibration function can then be determined, e.g., by performing a least squares linear fit, or linear fit using another metric. Any suitable regression analysis can be used.

Accordingly, the calibration function can be obtained using values from each of a plurality of other samples from other pregnant females. A first value of the fetal DNA concentration can be measured in the other sample, where the measurement of the fetal DNA concentration would not use an identification of mitochondrial DNA. Examples of such techniques are provided above. A second value can be measured of the normalized amount of the plurality of DNA molecules that are mitochondrial DNA using other sequence information obtained from the other sample. A two-dimensional data point from the first value and the second value can be determined for each samples, e.g., as in FIGS. 6 and 7. A regression analysis of the two-dimensional data points can be performed to obtain the calibration function.

At block 1150, the calibration function is used to estimate the fetal DNA concentration in the biological sample based on the measured amount. For example, using the example calibration function above, the normalized amount can be an input variable to the calibration function, which outputs the fetal DNA fraction. In other embodiments (e.g., where the calibration function is defined as a set of data points), an interpolation can be used between two calibration data points that have normalized amounts adjacent to the normalized amount being tested. The interpolated function can provide the fetal DNA fraction.

III. Cancer Detection

The measurement of mitochondrial DNA can also be used for the detection and monitoring of cancers. Some embodiment can perform a massively parallel sequencing of cell-free DNA fragments in a sample to obtain sequence reads, which can be mapped to a reference nuclear genome and a reference mitochondrial genome. The mapped reads can be used to measure a proportion/percentage (examples of a normalized amount) of the DNA fragments in the sample that are mitochondrial DNA. As shown below, when a normalized amount is determined in this manner, results below show that the normalized amount provides high accuracy in determining a level of cancer. Further, the results are consistent with the mitochondrial DNA content in the tissue in which the tumor exists.

Massively parallel sequencing can provide advantages of: (1) one can interrogate multiple parts or close to the entire mitochondrial genome; (2) one can use bioinformatics means to exclude mitochondrial genomic regions that are homologous to nuclear genomic sequences; (3) one can analyze sequences that are shorter than those typically detected using PCR-based assays; and (4) one could measure the relative amounts of nuclear and mitochondrial sequences using the same assay.

A. MtDNA % for Tumor and Blood Tissue

We analyzed the mitochondrial DNA content of certain tissues that can be found in a blood sample, including hematopoietic (blood) cells. As discussed above for maternal samples, the mitochondrial DNA content of the underlying tissues in a plasma sample (or other mixture with cell-free DNA) affects the overall mitochondrial DNA content in the sample.

To analyze the mitochondrial DNA content, we used hepatocellular carcinoma HCC. We sequenced the resected tumor tissues and peritumoral non-malignant tissues of 12 patients suffering from HCC. The sequencing was performed using the Illumina HiSeq series of sequencers as described above. Seventy-five nucleotides were sequenced for each of the two ends of each DNA fragment to be sequenced. Paired-end alignment to the reference sequence comprising of the reference human nuclear and mitochondrial genomes (hg19) using the SOAP2 program was performed.

Figure 12:
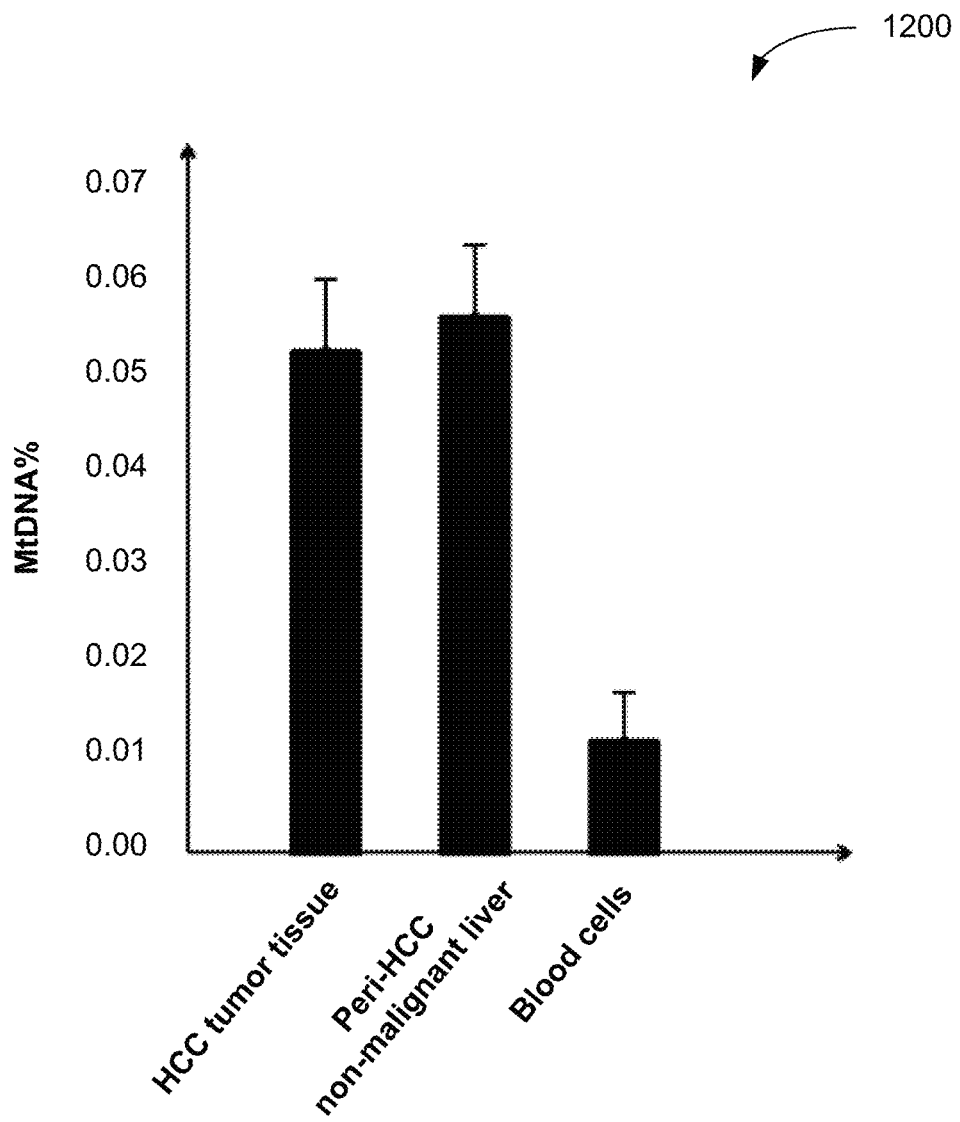
FIG. 12 shows a graph 1200 of the mean mitochondrial DNA percentage (MtDNA %) for HCC tumor tissues, peritumoral non-malignant liver tissues, and blood cells samples.

FIG. 12 shows a graph 1200 of the mean mitochondrial DNA percentage (MtDNA %) for HCC tumor tissues, peritumoral non-malignant liver tissues, and blood cells samples. The whiskers represent the standard deviations of the measurements. Compared with the blood cells, the HCC tumor tissues and the peri-tumoral non-malignant liver tissues had significantly higher mitochondrial DNA fractions (P<0.001 for both groups, Student t-test).

Graph 1200 shows that the tumor liver tissue and the non-malignant liver tissue have a comparable MtDNA %. As the liver contributes mitochondrial DNA (MtDNA) to plasma, the additional tumor tissue will add more DNA to the plasma relative to when no tumor exists. Because of the higher levels of mitochondrial DNA fraction in the HCC tumor tissues than in the blood cells, the presence of tumor-derived DNA in the plasma of HCC patients would lead to an increased concentration of mitochondrial DNA in plasma relative to the nuclear DNA.

B. MtDNA % in Plasma

We analyzed the plasma of various subjects with various liver conditions so as to illustrate the ability of embodiments to discriminate cancer from the other liver conditions using mitochondrial DNA content. Specifically, we analyzed the plasma of 90 HCC patients using massively parallel sequencing. Plasma samples from 67 subjects with chronic HBV infection, 36 subjects with HBV-associated cirrhosis and 32 healthy subjects were analyzed as controls.

Figure 13:
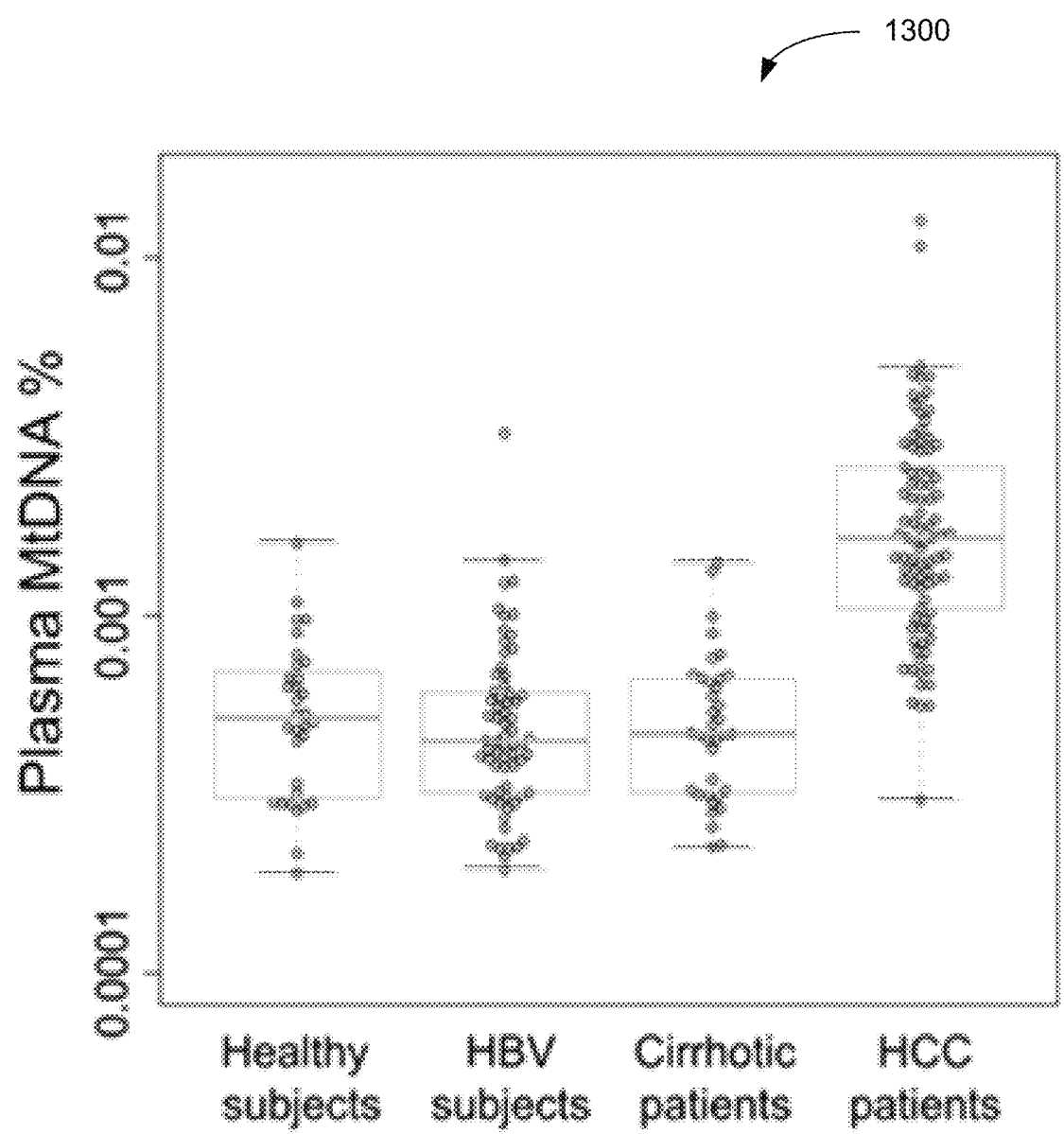
FIG. 13 shows a plot 1300 of plasma MtDNA % for healthy subjects, hepatitis B virus (HBV) subjects, cirrhotic patients, and HCC patients according to embodiments of the present invention.

FIG. 13 shows a plot 1300 of plasma MtDNA % for healthy subjects, HBV subjects, cirrhotic patients, and HCC patients according to embodiments of the present invention. An elevation of plasma mitochondrial DNA fraction was observed in the HCC patients compared with all the three groups of controls (P<0.001, Student t-test). The median fractional concentrations of mitochondrial DNA in plasma were 0.0014% and 0.00045% for the HCC patients and the healthy subjects, respectively (P-value<0.0001, Mann-Whitney test). The thick lines show the medians. The upper and lower bounds of the boxes show the interquartile range (i.e., between 25% and 75%). The whiskers show the $10^{th}$ and $90^{th}$ percentiles. Other plots use similar notations.

Plot 1300 shows that subjects with HCC can accurately be discriminated from healthy subjects and subjects with other liver conditions. Accordingly, the quantitative analysis of plasma mitochondrial DNA by massively parallel sequencing can serve as a marker for HCC. As discussed above, the higher MtDNA content relative to nuclear DNA can be measured in a variety of ways to provide a normalized amount for discriminating patients with cancer. The diagnostic accuracy of plasma mitochondrial DNA fraction for differentiating HCC patients and healthy controls is further illustrated using ROC curve analysis.

Figure 14:
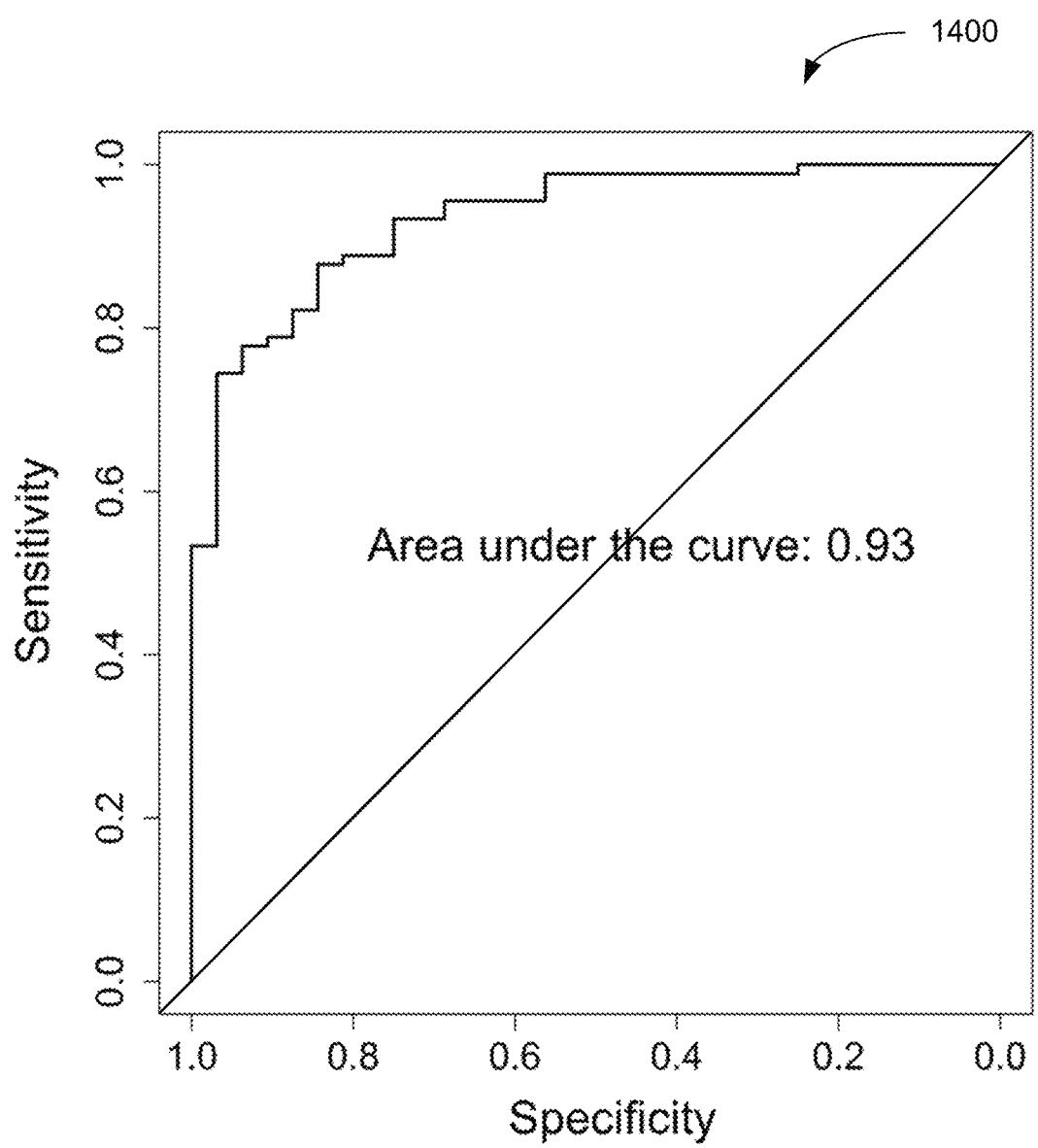
FIG. 14 is a plot 1400 showing a receiver operating characteristic (ROC) curve for the diagnostic accuracy of plasma mitochondrial DNA fraction for differentiating HCC patients and healthy controls according to embodiments of the present invention.

FIG. 14 is a plot 1400 showing a receiver operating characteristic (ROC) curve for the diagnostic accuracy of plasma mitochondrial DNA fraction for differentiating HCC patients and healthy controls according to embodiments of the present invention. The area under curve was 0.93. This indicates that the fraction of mitochondrial DNA in plasma is useful for the detection of HCC.

With a cutoff of 0.00084%, as determined by the top left-hand point of the ROC curve, a sensitivity of 80% and a specificity of 94% were achieved for discriminating HCC patients and healthy subjects. No significant difference in the fractional concentration of mitochondrial DNA was observed between the HBV carriers (P-value=0.32, Mann-Whitney test) or patients with liver cirrhosis (P-value=0.49, Mann-Whitney test) when compared with the healthy subjects.

Figure 15:
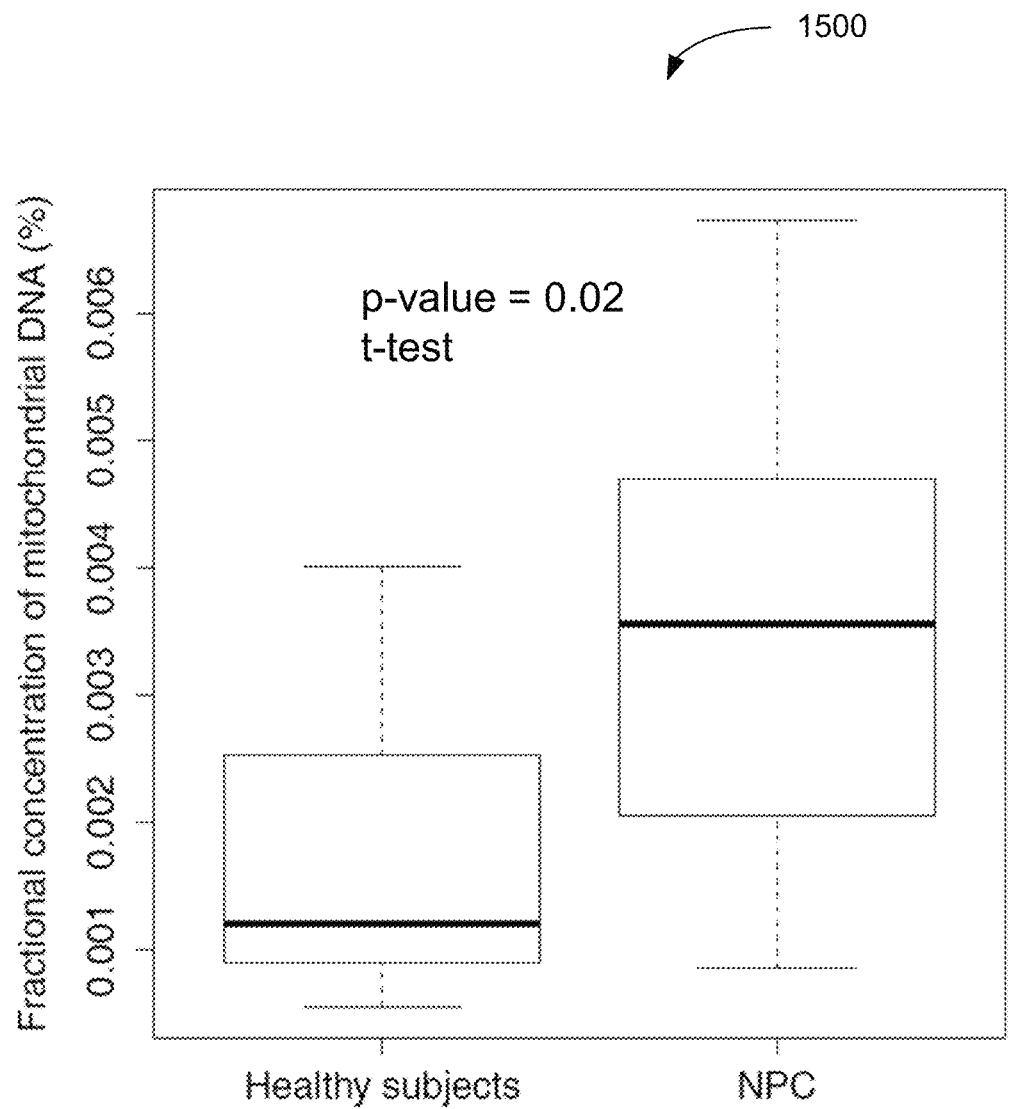
FIG. 15 shows a plot 1500 of plasma MtDNA % for healthy subjects and NPC (nasopharyngeal cancer) patients according to embodiments of the present invention.

FIG. 15 shows a plot 1500 of plasma MtDNA % for healthy subjects and NPC (nasopharyngeal cancer) patients according to embodiments of the present invention. The fractional concentration of mitochondrial DNA in plasma of NPC (nasopharyngeal cancer) patients is twice as high as healthy subjects. This NPC data further shows that MtDNA % can be used to discriminate between subjects with cancer and subjects without cancer. A suitable threshold can be selected for such a discrimination based on plots like plot 1500. For example, a threshold of 0.003 can provide a high specificity, with relatively few false positives. Such a threshold is an example of a reference value that is based on reference samples (healthy subjects in this case).

Further examples of using normalized amounts of MtDNA in a comparison to a reference value are now discussed. The comparison can determined whether the amount is statistically different (e.g., above or below) the reference value. When the reference value corresponds to value from reference samples, a threshold for the difference can be used, e.g., corresponding to a standard deviation of three for the difference, as seen in a distribution of values seen in a population.

A normalized amount for the MtDNA can be calculated by dividing the number of sequence reads aligning to the MtDNA genome by the total number of sequence reads alignable to either genome. This normalized amount allows results from one sample to be compared to the results of another sample. For example, the normalized amount can be the proportion (e.g., percentage or fraction) of sequence reads, where the reference value is the value expected to be from the MtDNA genome for a healthy subject or a subject with cancer. But, many other normalizations are possible, as would be apparent to one skilled in the art. For example, one can normalize by dividing the number of MtDNA sequence reads by the number of nuclear sequence reads or by always using a same number of sequence reads. This normalized amount can then be compared against a threshold value, which may be determined from one or more reference samples not exhibiting cancer.

In some embodiments, the threshold value can be the reference value. In other embodiments, the comparison can include the reference value and the threshold value. For example, the comparison can include a separation value (e.g., ratio or difference) between the normalized amount and the reference value, and the separation value can be compared to a threshold value to see if a statistically significant difference exists.

In one embodiment, the comparison is made by calculating a z-score using the following equation: z-score=(normalized amount of the case−mean)/S.D., where "mean" is the mean normalized amount for the reference samples; and S.D. is the standard deviation of the normalized amount for the reference samples. Hence, the z-score can correspond to the number of standard deviations that the normalized amount for the tested case is away from the mean normalized amount of the one or more reference subjects. This z-score can be compared to a threshold.

C. Tumor Size

The magnitude of the normalized amount can be determined by several factors. One factor is the MtDNA content of the tumor tissue and the fractional concentration of tumor-derived DNA in the biological sample (e.g. plasma). A higher MtDNA content of the tumor tissue increases the amount of cell-free MtDNA released from the tumor. If the tumor tissue has a higher MtDNA content than blood cells, the relative amount of MtDNA to nuclear DNA will increase. And, the higher the fractional concentration of tumor-derived DNA in the sample (e.g. plasma), the larger the normalized amount of the tested case when the tumor tissue has a higher MtDNA content than blood cells.

To analyze a change in normalized amount, the plasma MtDNA % was measured for patients that had a tumor whose size and tissue-type had been determined, e.g., via surgery. The concentration of MtDNA in the tissue-type of the tumor was also measured.

Figure 16:
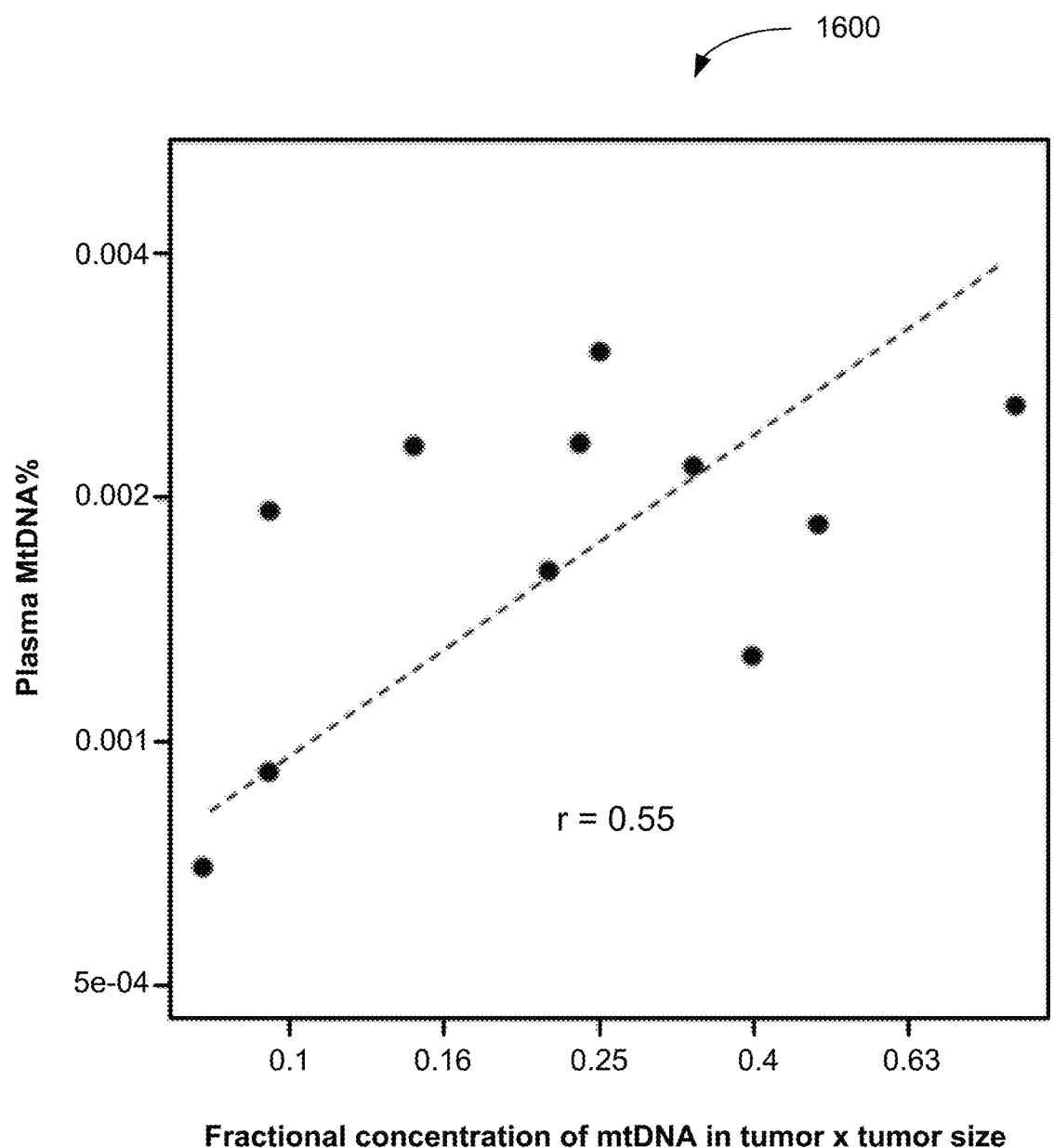
FIG. 16 shows a plot 1600 of the fraction of mitochondrial DNA in plasma plotted against the product of the fractional concentration of mitochondrial DNA in the tumor tissue and tumor size according to embodiments of the present invention.

FIG. 16 shows a plot 1600 of the fraction of mitochondrial DNA in plasma plotted against the product of the fractional concentration of mitochondrial DNA in the tumor tissue and tumor size according to embodiments of the present invention. A positive relationship was observed (R=0.55, Pearson correlation). Accordingly, an increase of MtDNA % for a given tumor tissue corresponds to an increase in a size of the tumor.

This relationship can be useful for the monitoring of disease progression, particularly after treatment. For a particular patient, the mitochondrial DNA fraction in the tumor tissue would be the same. Therefore, the serial changes in the mitochondrial DNA fraction in plasma would be useful to reflect the tumor size. Thus, embodiment can track a size of a tumor over time based on the plasma fractional concentration of mitochondrial DNA.

The function in plot 1600 is another example of a calibration function. In this example, the calibration function can provide a tumor size when the MtDNA content in the source tissue is known. The size of a tumor is an example of a classification of a level of cancer. The discussion above for calibration functions also applies to this example and other regression analyses described herein.

Additionally, as the tumor size is proportional to the tumor DNA fraction, the tumor DNA fraction can be determined based on mitochondrial DNA fraction for a given tumor. For example, reference samples of patients with various sizes of tumors can have a tumor DNA fraction measured. Then, once a tissue-type of a tumor is known and the size of the tumor is estimated, say by imaging methods like CT scan, the % MtDNA in plasma can be used to determine the tumor DNA fraction.

In addition to the detection and monitoring of primary cancers, the analysis of mitochondrial DNA in plasma may also be applied for the detection of metastatic cancers. Metastatic cancer may cause significant tissue destruction in the metastatic organ. For example, colorectal cancers metastasized to the liver can cause significant destruction of liver tissues. As liver tissues have a higher fraction of mitochondrial DNA than both blood cells and colorectal tissues, elevation of mitochondrial DNA in plasma can be useful for indicating the presence of metastatic disease in the liver.

Figure 17:
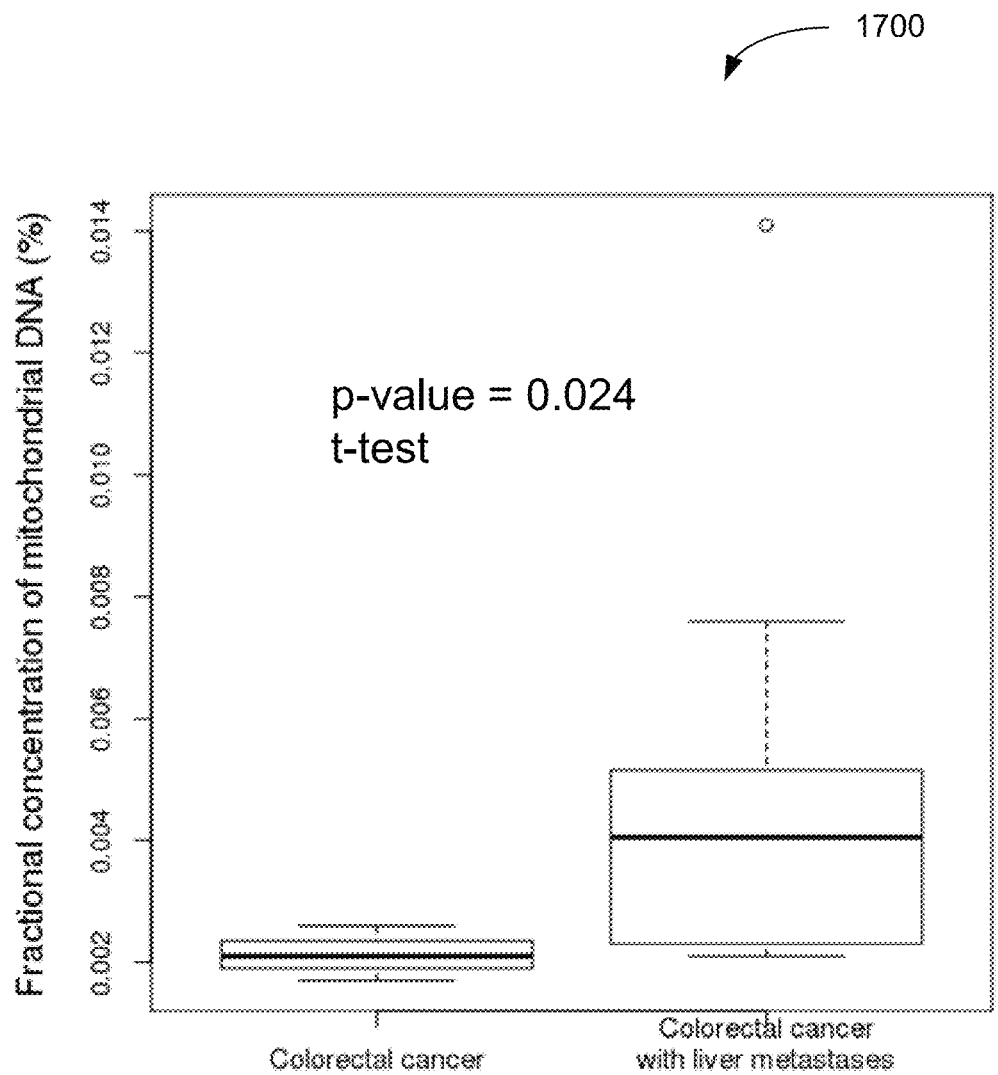
FIG. 17 shows a plot 1700 of plasma MtDNA % for colorectal cancer patients and colorectal cancer patients with liver metastases according to embodiments of the present invention.

FIG. 17 shows a plot 1700 of plasma MtDNA % for colorectal cancer patients and colorectal cancer patients with liver metastases according to embodiments of the present invention. The fractional concentration of mitochondrial DNA in plasma of colorectal cancer with liver metastasis subjects is 2.2 fold greater than colorectal cancer without metastases. Accordingly, a threshold of about 0.0025 can be used to discriminate between patients with colorectal cancer and patients with colorectal cancer with liver metastases. Based on the present disclosure, one skilled in the art would be able to determine other thresholds for discriminating between other cancers and metastases.

Accordingly, in some embodiments, if a patient had one type of cancer, and then the normalized amount drastically shot up, then one could identify that the cancer had metastasized to a tissue with higher mitochondria per cell. For example, there are only ~150 copies of MtDNA in colon tissue. Therefore, the increase of MtDNA would not be too big without liver metastasis. However, the involvement of the liver would likely lead to a much higher level of MtDNA in plasma because of the much higher level of MtDNA in liver.

D. Size Profile of Mitochondrial DNA for Cancer

Mitochondrial DNA was suspected to be shorter as it was also not wound around a histone. Thus, MtDNA would suffer greater pressure of degradation and enzymatic cleavage, and thus be shorter. As the number of sequenced mitochondrial DNA fragments was relatively small for any individual subject, we pooled the sequenced mitochondrial DNA fragments from all subjects in the same group to obtain a pooled size profile.

Figure 18:
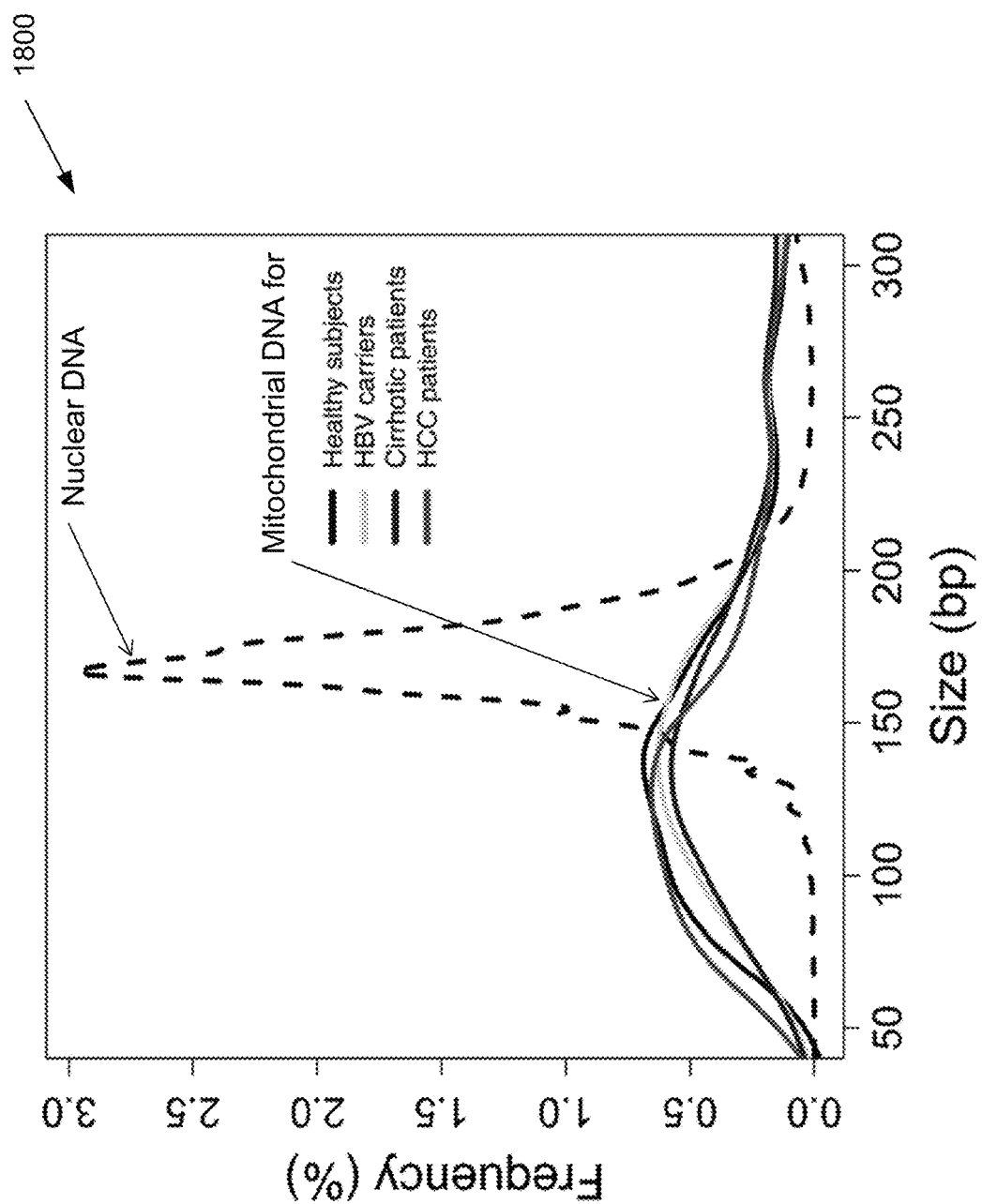
FIG. 18 shows the size profiles of circulating mitochondrial DNA in healthy subjects (black), HBV carriers (yellow), cirrhotic patients (blue) and HCC patients (red). The size profile of circulating nuclear DNA of one healthy control subject is shown for comparison (dotted line).

FIG. 18 shows the size profiles of circulating mitochondrial DNA in healthy subjects (black), HBV carriers (yellow), cirrhotic patients (blue) and HCC patients (red). The size profile of circulating nuclear DNA of one healthy control subject is shown for comparison (dotted line).

Circulating nuclear DNA showed a characteristic size pattern with a prominent peak at 166 bp. This pattern is likely to be the result of protection from enzymatic degradation due to histone binding to nuclear DNA. This pattern was not observed in the size distribution of circulating mitochondrial DNA. We also observed that the size distribution of mitochondrial DNA was shorter than that of nuclear DNA in plasma.

One can determine an expected amount of mitochondrial DNA in a sample based on an average number of mitochondria in cells, along with the known length of the mitochondrial DNA for one mitochondrion (i.e., 16 kb). For healthy subjects, the measured amount of mitochondrial DNA in plasma was lower than expected amount (i.e., based on the length of the mitochondrial DNA in a number of mitochondria). For cancer patients, the measured amount was higher than expected amount by an order of magnitude.

The median fractional concentration of plasma mitochondrial DNA was only 0.00045% in healthy subjects. This fractional concentration is relatively low considering that the size of mitochondrial genome is 0.00053% of the size of the nuclear genome and that there are 50 to 4,000 mitochondria per cell (Kelly R D et al. Mitochondrial DNA copy number is regulated in a tissue specific manner by DNA methylation of the nuclear-encoded DNA polymerase gamma A. *Nucleic Acids Res* 2012; 40(20):10124-10138; and Mengel-From J, et al. Mitochondrial DNA copy number in peripheral blood cells declines with age and is associated with general health among elderly. *Hum Genet* 2014; 133(9):1149-1159).

The smaller size distribution and relatively low abundance of circulating mitochondrial DNA is likely to be due to the higher susceptibility of mitochondrial DNA to degradation due to the absence of histone protection. As noted above, the concentration of mitochondrial DNA in plasma was higher in the HCC patients compared with the healthy subjects. This may be due to the higher number of mitochondria in HCC cells or liver cells in general when compared with hematopoietic cells, which are the major source of circulating DNA in healthy subjects (Kelly R D et al. (2012); Mengel-From J, et al. (2014); and Lui Y Y N, et al. Predominant hematopoietic origin of cell-free DNA in plasma and serum after sex-mismatched bone marrow transplantation. *Clin Chem* 2002; 48(3):421-427).

Further, for cancer cells, there is more mitochondrial DNA. The overall size of the DNA (nuclear and mitochondrial) will be less, given a higher proportion of mitochondrial DNA for cancer patients. Thus, a higher proportion of mitochondrial DNA for cancer patients would affect the overall size profile. But because the stability of MtDNA in plasma is much lower than that of nuclear DNA, the actual amount of sequence reads from MtDNA is extremely low. The tumor DNA fraction has a bigger impact on the overall size profile because the degree of shortening among the tumor DNA is more profound and the tumor DNA fraction is higher than the MtDNA fraction.

The size distribution of the circulating mitochondrial DNA molecules can affect the accuracy to detect the MtDNA using certain techniques. As shown in FIG. 18, the circulating mitochondrial DNA molecules were fragmented to below 150 bp. The sensitivity of PCR is dependent on the size of the target fragments. The shorter the template DNA, the lower the probability that the fixed PCR primers can span the whole DNA molecule and to detect it. In contrast, in massively parallel sequencing, sequencing primers are normally added to the ends of the target molecule. Therefore, the probability of a molecule being sequenced is less adversely affected by the shorter size profile of the DNA molecules, thereby providing consistent and accurate results.

E. Method

Figure 19:
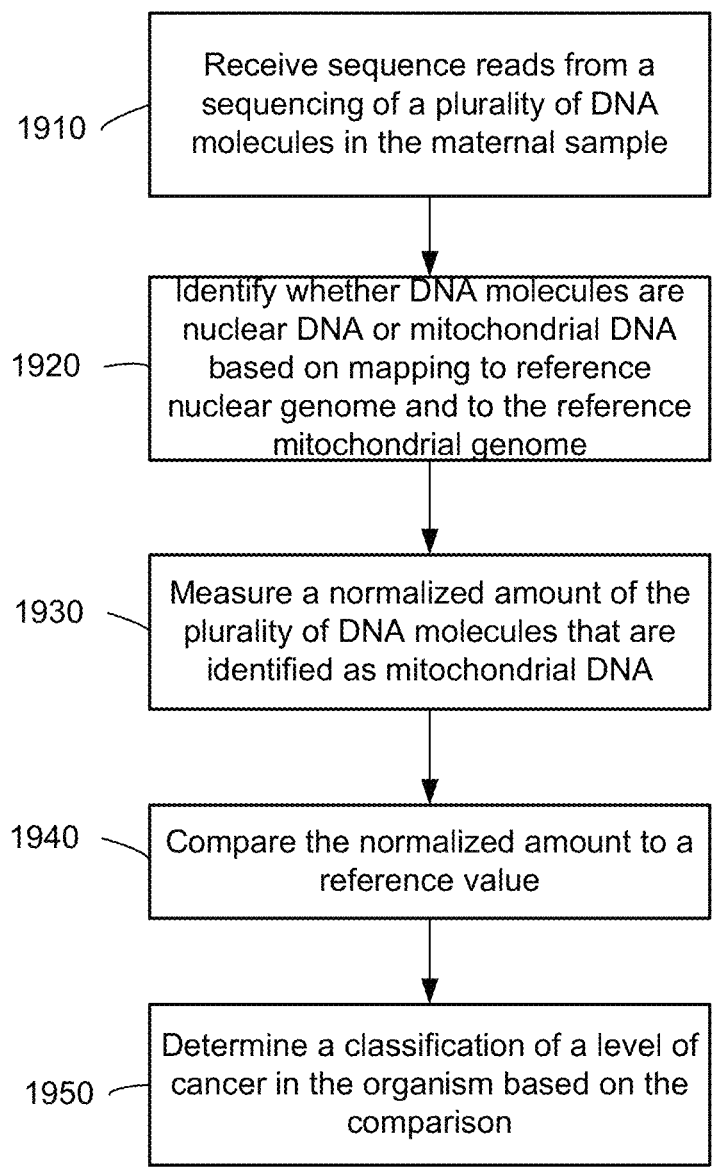
FIG. 19 is a flowchart illustrating a method 1900 of analyzing a biological sample of an organism to determine a classification of a level of cancer of the organism using an amount of mitochondrial DNA in the biological sample according to embodiments of the present invention.

FIG. 19 is a flowchart illustrating a method 1900 of analyzing a biological sample of an organism to determine a classification of a level of cancer of the organism using an amount of mitochondrial DNA in the biological sample according to embodiments of the present invention. The biological sample includes cell-free DNA molecules originating from normal cells and potentially from cells associated with cancer. The cell-free DNA of the biological sample include mitochondrial DNA and nuclear DNA. As examples, the biological sample can be plasma or serum.

At block 1910, sequence reads from a sequencing of a plurality of DNA molecules in the biological sample is received at a computer system. The sequencing can be a random sequencing of DNA molecules, e.g., a sequencing can be performed using adaptors. Other embodiments can use random sets of primers, e.g., an exhaustive set so that all sequences have a matching primer. A complete set of random hexamers can be used.

At block 1920, for each of a plurality of DNA molecules in the biological sample, it is determined whether the DNA molecule is nuclear DNA or mitochondrial DNA. The location of the DNA molecule can be determined in a reference nuclear genome or a reference mitochondrial genome using the sequence reads for the DNA molecule. In one implementation, a mapping of a corresponding sequence read can be attempted to the reference nuclear genome and to the reference mitochondrial genome. In one example, only uniquely mapped reads are used.

In attempting to map the DNA molecules to the reference nuclear genome and to the reference mitochondrial genome, embodiments can perform a first mapping procedure using one or more first criteria for determining a first alignment to the reference mitochondrial genome. The one or more first criteria can specify a number of allowed mismatches, a number of locations that are allowed for matching, and whether all of the reference genomes are used for mapping. In one embodiment, mapping the DNA molecules uses at least a majority of the reference nuclear genome and the reference mitochondrial genome.

For each sequence read that is determined to align to the reference mitochondrial genome based on the first mapping procedure, a second mapping procedure can be performed to the reference nuclear genome and to the reference mitochondrial genome using one or more second criteria that are more stringent than the one or more first criteria. In one implementation, a sequence read contributes to the normalized amount only if the sequence read maps to the mitochondrial genome for the first and second mapping procedures. For example, the one or more second criteria can include that the sequence read maps to a unique position on the reference mitochondrial genome and/or has fewer mismatches than allowed in the first mapping procedure. Whereas, the first mapping procedure can allow more mismatches and/or more locations for matching. The one or more second criteria can also include that the sequence read aligns to the reference mitochondrial genome with fewer mismatches than a second alignment to the reference nuclear genome. The initial pass at the mapping can be quicker so as to identify potential sequence reads that are for MtDNA, and then only spend more computational time after the sequence read potentially aligns to the MtDNA.

In some embodiments, a sequence read is counted as corresponding to nuclear DNA when the first mapping procedure does not identify a potential alignment to the reference mitochondrial genome. In this manner, only the MtDNA have to be explicitly mapped to both the reference nuclear genome and the reference mitochondrial genome. Accordingly, as there is considerable homology between the mitochondrial genome and the nuclear genome, all sequenced reads that were initially mapped to the mitochondrial genome can be realigned to a combined nuclear and mitochondrial genome using a more stringent requirement of mapping accuracy. Such a technique can be performed for any of the methods described herein.

At block 1930, a normalized amount of the plurality of DNA molecules that are identified as mitochondrial DNA is measured. Block 1930 can be performed in a similar manner as block 1130 of method 1100. Accordingly, the normalized amount can be relative to a second amount of the plurality of DNA molecules including DNA molecules that are identified as nuclear DNA molecules. As examples, the second amount could be of nuclear and mitochondrial DNA molecules or just the nuclear DNA molecules.

For massively parallel sequencing, many more targets can be generated from the same number of mitochondrial genomes. For PCR, only a single or a few targets on the mitochondrial genome are detected. Assuming that a mitochondrial genome is fragmented into fragments of 150 bp, one mitochondrial genome would be fragmented to 106 fragments. This higher number of target molecules would translate into a better sensitivity and precision for quantification.

At block 1940, the normalized amount is compared to a reference value. As an example, the reference value could be a threshold value determined for normal samples. As mentioned above, the comparison may include determining a z-score (or other difference or ratio, or function of such) based on the normalized amount and the reference value, and comparing the result to a threshold. In other embodiments, the reference value can include the threshold value, e.g., if the other values in the z-score were moved to the other side of the equation.

At block 1950, a classification of a level of cancer in the organism is determined based on the comparison. As examples, the classifications can include positive for cancer, negative for cancer, or indeterminate. More than one reference value can be used to determine which of the classifications applies. For example, a reference value can exist for discriminating between either of two classifications.

Further examples of classifications can include a size of a tumor (FIG. 16) or a stage of cancer, e.g., whether the cancer as metastasized (FIG. 17). Thus, a reference value can be determined from a calibration function (e.g., calibration data points) so as to determine the classification of size. A nearest calibration value to the measured normalized amount can be conserved the reference value, in one example. When a tumor is in a tissue with less MtDNA content than blood cells, cancer can be detected when the normalized amount is less than a threshold. In such a manner, different tissues can be ruled out as the source of the tumor based on whether the normalized amount is above or below the threshold.

Per the description above, a threshold of MtDNA abundance can be used to distinguish an HCC patient from a normal subject. The threshold can be established from a group of healthy normal subjects. In one example, sixteen healthy normal subjects were used to determine the normal reference range based on the mean and standard deviation (SD). Two SDs above the mean of healthy controls was deemed to indicate significant overrepresentation of mitochondrial DNA in plasma. In order to minimize the influence of those ambiguous reads which can be mapped to both human nuclear and mitochondrial genome due to the homologous regions, we compiled mitochondrial and human genomes together to form a single database. Only the reads which were aligned uniquely to mitochondrial genome were used for down-stream analysis. By making the mitochondrial and human genomes available for alignment concurrently, DNA fragments that derived from the homologous regions would be alignable to more than one region of the combined genome. When only DNA fragments or sequence reads that uniquely align to only one location in the combined genome were selected, those DNA molecules that originate from the homologous regions were discarded. Using this approach, a sensitivity of 80% was achieved when the specificity was 93%. On the other hand, when the sequence data are aligned exclusively to the mitochondrial genome inclusive of the homologous regions, the sensitivity was only 51% when the specificity was 93%.

IV. Auto-Immune Detection Using Mitochondrial DNA

Mitochondrial DNA (MtDNA) can also be used for the detection of auto-immune diseases, such as systemic lupus erythematosus (SLE). Elevated levels of MtDNA in plasma are also seen for auto-immune diseases, given that the cells being attacked would generally have a higher concentration of MtDNA than blood cells.

A. SLE

Systemic lupus erythematosus (SLE) is an autoimmune disease which is caused by the 'self-attack' by the immune system against the body and results in inflammation and tissue damage. Unlike other autoimmune diseases such as multiple sclerosis and type 1 diabetes mellitus, SLE is considered to be a prototypic systemic autoimmune disease. It has the potential of affecting multiple organ systems including the skin, muscles, bones, lungs, kidneys, cardiovascular and central nervous systems.

SLE is characterized by the loss of immunologic self-tolerance and production of autoantibodies. Serum anti-double-stranded (ds) DNA antibody titer of SLE patients is used as a serologic means to assess the disease activity. However, about 30% SLE patients are negative for this test even during the active stage.

Figure 20:
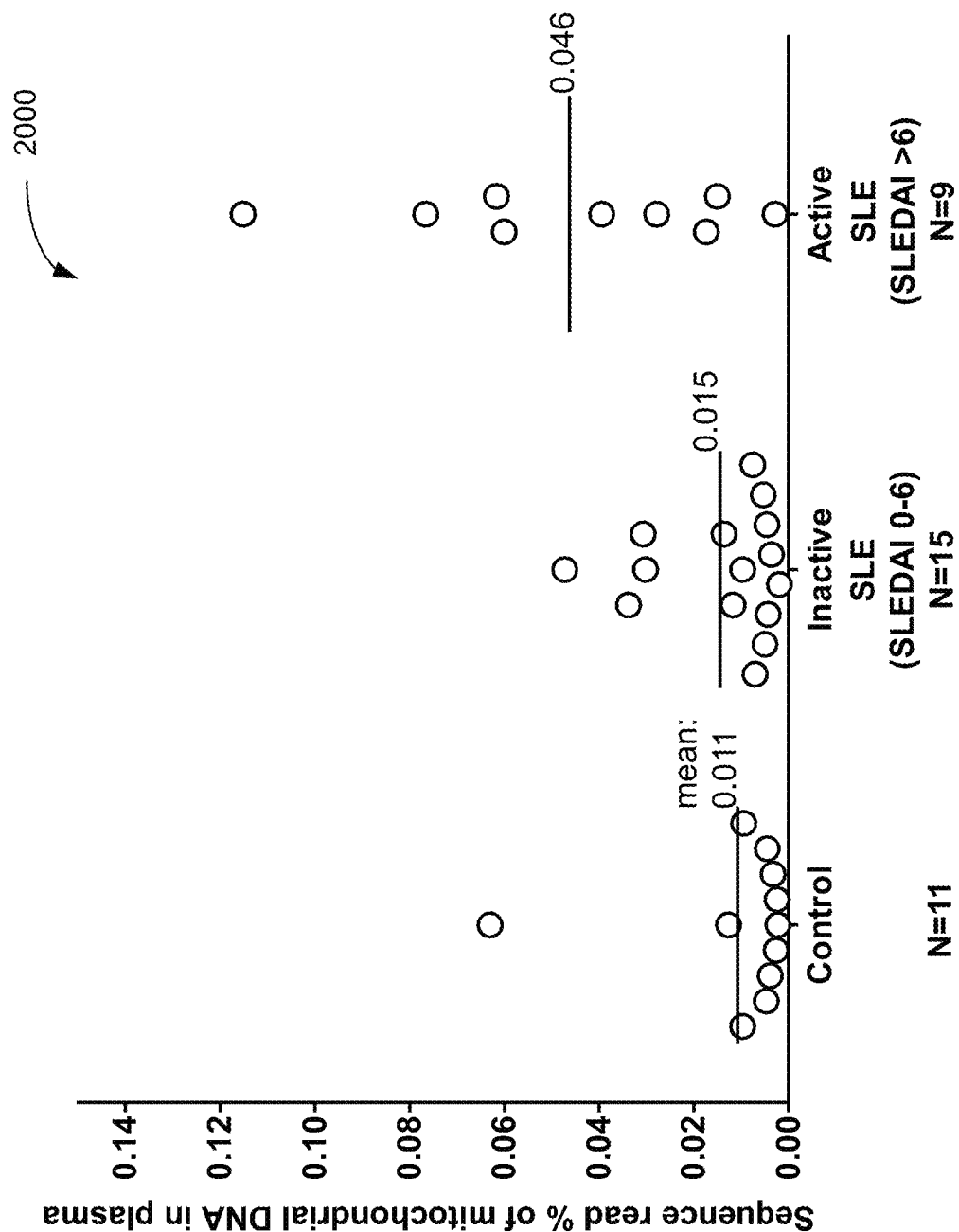
FIG. 20 is a graph 2000 showing a percentage of sequence reads in a plasma sample that are of mitochondrial DNA (MtDNA) among different groups according to embodiments of the present invention.

The acceleration of cell death and impairment of clearance of the by-products of the dead cells associated with SLE may generate extra-cellular DNA and change the characteristics of DNA in the circulation of SLE patients. In addition, other mechanisms involved in the pathogenesis of SLE, such as the deficiency of DNase activity and overproduction of autoantibodies against DNA, can also alter the integrity of circulating DNA. As shown below, the immune dysregulation of SLE can change the MtDNA % in a sample (e.g., plasma) of SLE patients B. Using MtDNA % to Determine Level FIG. 20 is a graph 2000 showing a percentage of sequence reads in a plasma sample that are of mitochondrial DNA (MtDNA) among different groups according to embodiments of the present invention. The different groups of patient include control patients, inactive SLE patients, and active SLE patients. There were 11 control patients, 15 inactive SLE patients, and 9 active SLE patients. The inactive LSE patients had a systemic lupus erythematosus disease activity index (SLEDAI) of 0-6 (Bombardier et al., Derivation of the SLEDAI. A disease activity index for lupus patients. The Committee on Prognosis Studies in SLE. Arthritis Rheum 1992, 35:630-640). The active LSE patients had a SLEDAI of greater than 6.

The active SLE group had a mean percentage of MtDNA that is 4.2 times and 3 times higher than controls (P=0.0057) and inactive SLE (P=0.0148), respectively. Thus, the active SLE patients can be discriminated from the control and inactive patients, e.g., using a threshold of 0.04 or other cutoff(s) identified by receiver-operating characteristic curve analysis or other suitable techniques, as will be known to one skilled in the art. The same data was also analyzed for SLEDAI and anti-ds DNA antibody level.

Figure 21:
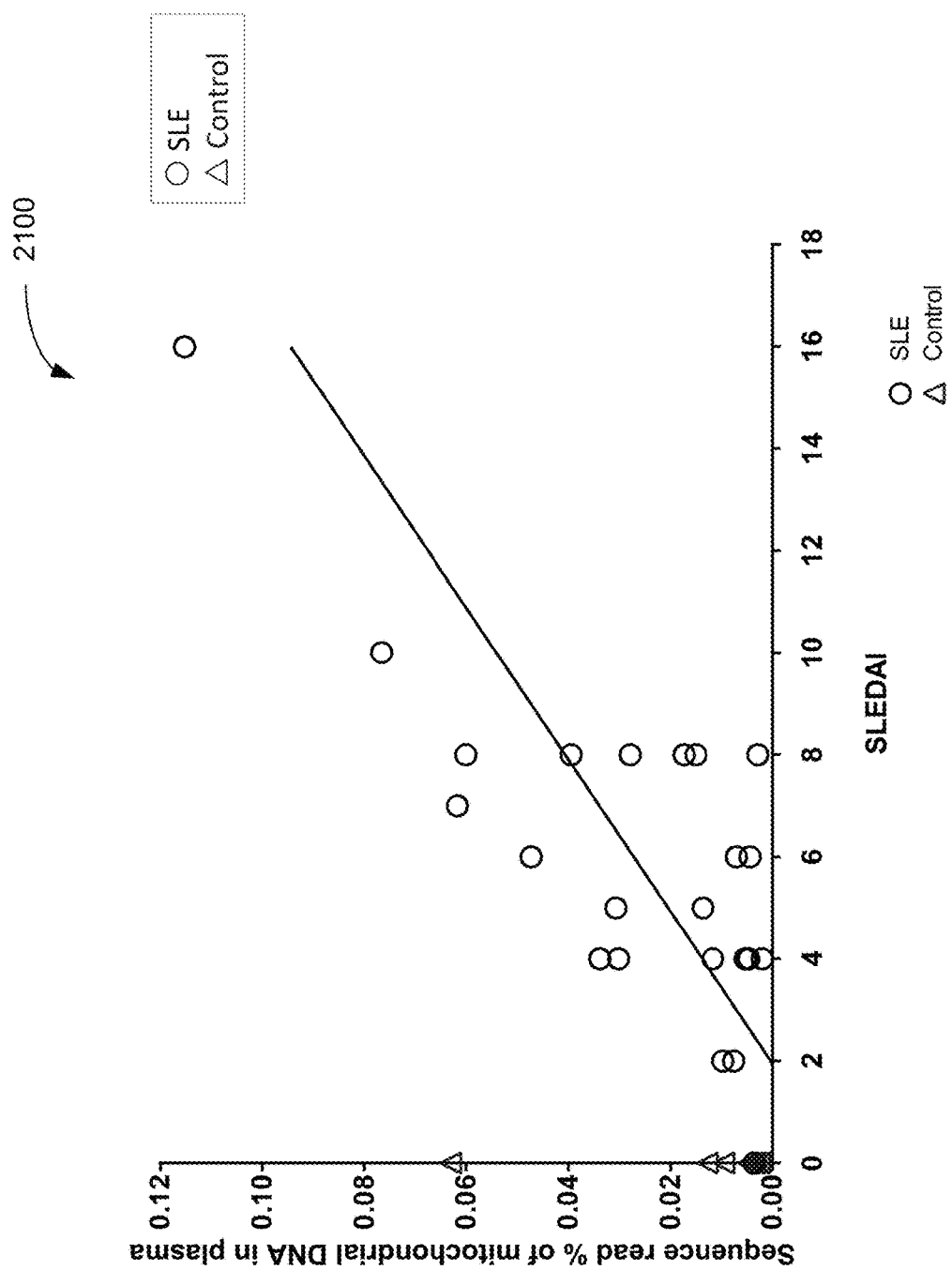
FIG. 21 is a plot 2100 showing the sequence read percentage of MtDNA in a plasma sample vs. SLEDAI according to embodiments of the present invention.

FIG. 21 is a plot 2100 showing the sequence read percentage of MtDNA in a plasma sample vs. SLEDAI according to embodiments of the present invention. The 11 control samples are shown as having SLEDAI of zero. Plot 2100 shows a correlation between the percentage of sequence reads of mitochondrial DNA in plasma and SLEDAI with Spearman's R=0.56 and P=0.0048. Only the SLE cases were used in determining the correlation values.

The linear fit (or other calibration function) can be used to determine a SLEDAI value based on the MtDNA %. The calibration function can be stored and determined in a similar manner as other calibration functions described herein. In this manner, the MtDNA % can be used to estimate a severity level of the SLE. A higher MtDNA % would indicate a higher severity level of SLE.

FIG. 21 also shows that a threshold of 0.02 can be used to discriminate between healthy patients and SLE patients. In some embodiments, a SLEDAI and a MtDNA % can be used, where SLEDAI can be determined through an independent process not involving MtDNA %. For example, to enhance specificity, both the MtDNA % and SLEDAI can be compared to respective thresholds to determine whether both are elevated. The criterion of both being elevated can be used to determine whether the auto-immune disease is present or to determine a severity. Thus, in some implementations, the existence of the auto-immune disease can be identified when either is elevated, but not identified as severe unless both are elevated. MtDNA % can be used to identify existence of the auto-immune disease, and SLEDAI used to determine severity. To enhance sensitivity, embodiments can identify an existence of the auto-immune diseased with either one is elevated. The thresholds for satisfying this criterion (i.e. either one being elevated) can be higher than for both needing to be elevated. Various threshold values can be used for both MtDNA % and SLEDAI to determine various severity levels.

Figure 22:
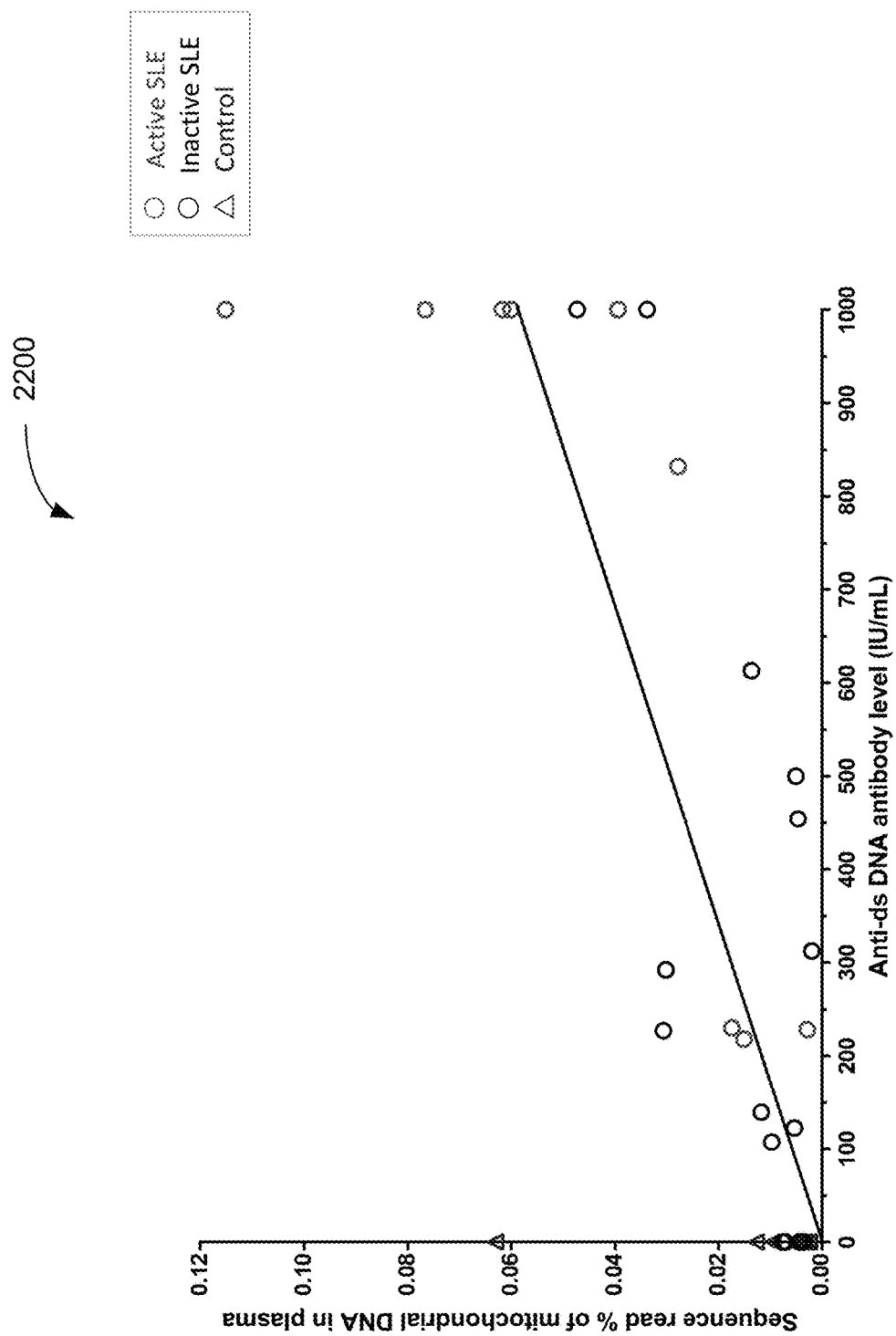
FIG. 22 is a plot 2200 showing the sequence read percentage of MtDNA in a plasma sample vs. anti-ds DNA antibody level according to embodiments of the present invention.

FIG. 22 is a plot 2200 showing the sequence read percentage of MtDNA in a plasma sample vs. anti-ds DNA antibody level according to embodiments of the present invention. The anti-ds DNA antibody level has been shown to be related to SLE (Isenberg et al. Detection of cross-reactive anti-DNA antibody idiotypes in the serum of systemic lupus erythematosus patients and of their relatives. Arthritis Rheum 1985; 28:999-1007). Plot 2200 shows a correlation between the percentage of sequence reads of mitochondrial DNA in plasma and anti-ds DNA antibody level with Spearman's R=0.71 and P<0.0001. All the SLE cases were used in determining the correlation values. As one can see the anti-body level does not always discriminate between active and inactive SLE. Using the anti-body level in combination with the MtDNA % can help to discriminate, e.g., the active SLE cases at 1000 anti-body level have higher MtDNA %. For example, a threshold of about 0.055 could be used. Thus, different MtDNA % thresholds can be selected and used for different anti-body levels (or ranges of levels) to increase accuracy.

Figure 23:
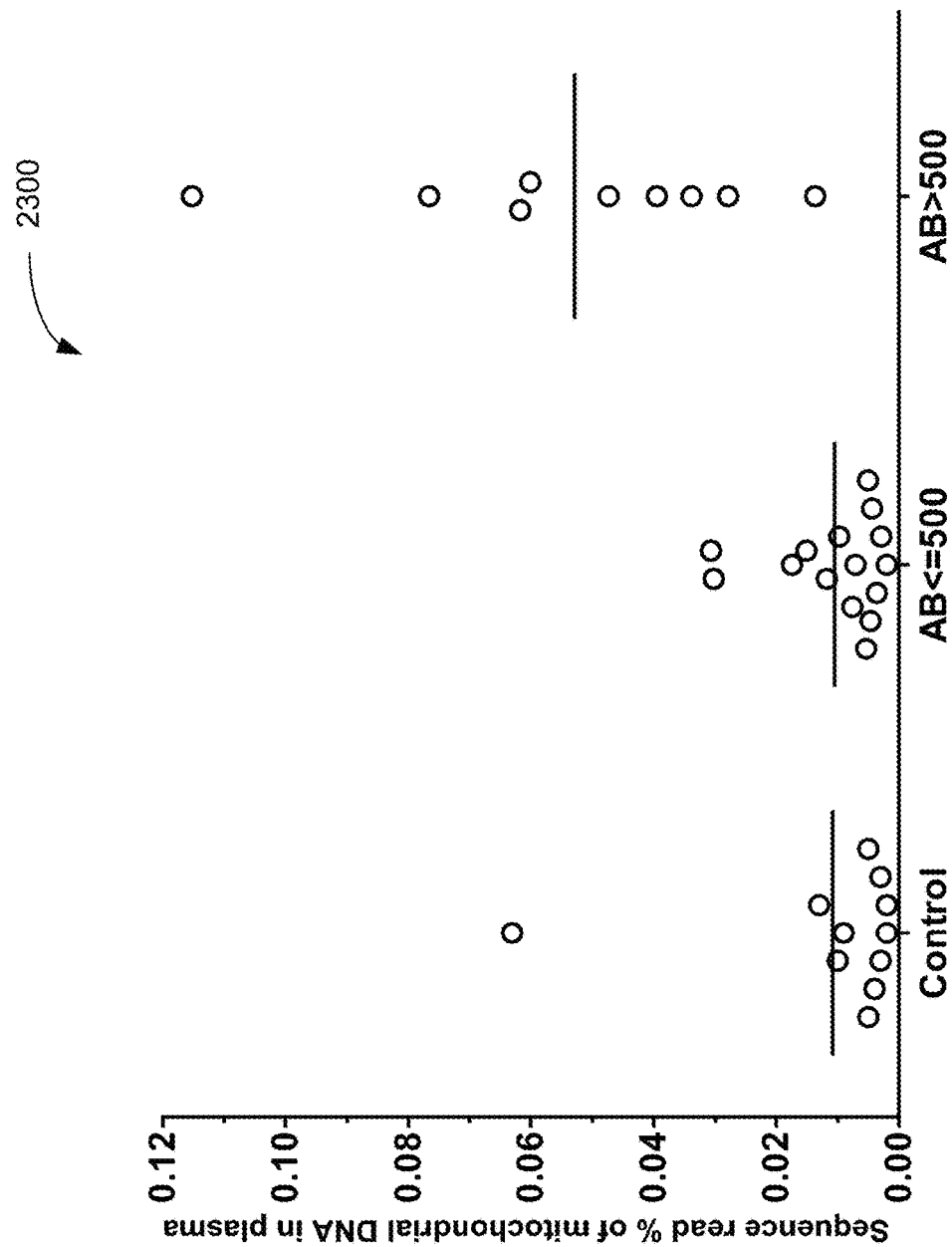
FIG. 23 is a graph 2300 showing the sequence read percentage of MtDNA in a plasma sample for various groups according to embodiments of the present invention.

FIG. 23 is a graph 2300 showing the sequence read percentage of MtDNA in a plasma sample for various groups according to embodiments of the present invention. In graph 2300, AB corresponds to the anti-ds DNA antibody level. The various groups are a control group (no SLE), a group with AB≤500, and a group with AB >500. As can be seen, the samples with AB>500 have a higher average MtDNA % than the control and the group with AB≤500. Accordingly, MtDNA % can discriminate in a similar manner as the anti-body level, as is also shown in FIG. 22. And, a combination of the two markers can be used.

C. Method

Figure 24:
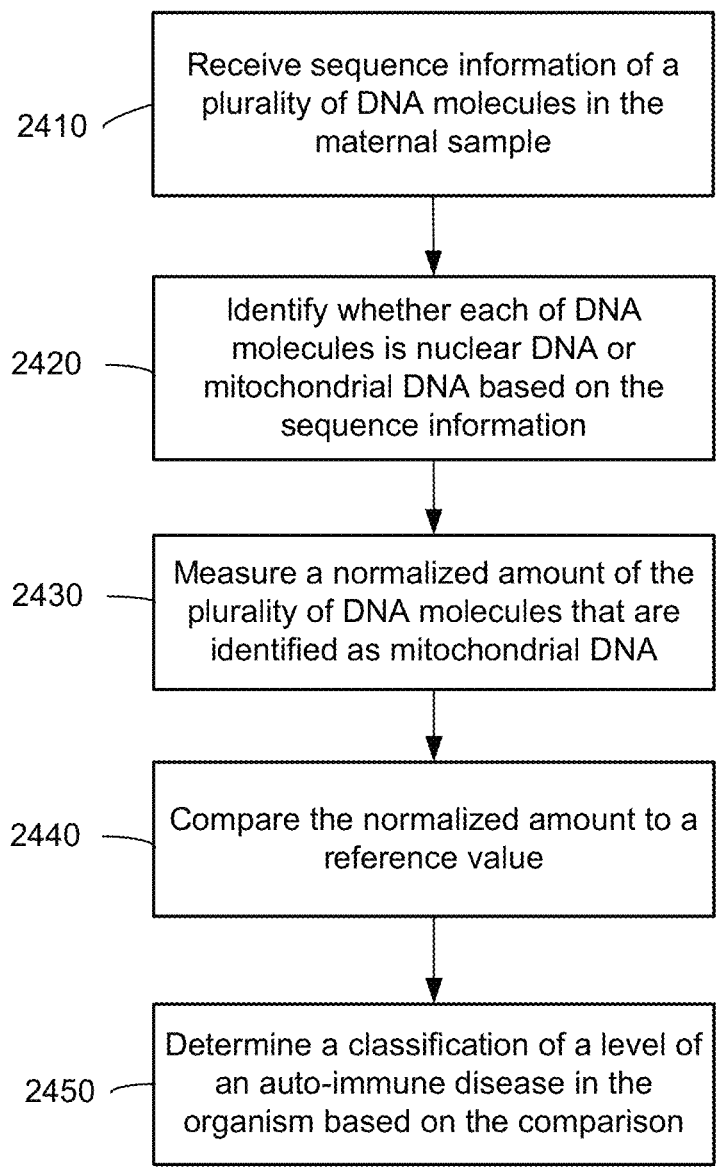
FIG. 24 is a flowchart illustrating a method 2400 of analyzing a biological sample of an organism to determine a classification of a level an auto-immune disease in the organism using an amount of MtDNA according to embodiments of the present invention.

FIG. 24 is a flowchart illustrating a method 2400 of analyzing a biological sample of an organism to determine a classification of a level an auto-immune disease in the organism using an amount of MtDNA according to embodiments of the present invention. The biological sample includes cell-free DNA. The cell-free DNA of the biological sample include mitochondrial DNA and nuclear DNA. As examples, the biological sample can be plasma or serum.

At block 2410, sequence information of a plurality of DNA molecules in the biological sample is received at a computer system. Block 2410 can be performed in a similar manner as block 1110 of method 1100.

At block 2420, for each of a plurality of DNA molecules in the biological sample, it is determined whether the DNA molecule is nuclear DNA or mitochondrial DNA. The location of the DNA molecule can be determined in a reference nuclear genome or a reference mitochondrial genome using the sequence information for the DNA molecule, e.g., by performing a mapping procedure of a sequence read to the reference nuclear genome and reference mitochondrial genome. Block 2420 can be performed in a similar manner as block 1120 of method 1100.

At block 2430, a normalized amount of the plurality of DNA molecules that are identified as mitochondrial DNA is measured. Block 2430 can be performed in a similar manner as block 1130 of method 1100. Accordingly, the normalized amount can be relative to a second amount of the plurality of DNA molecules including DNA molecules that are identified as nuclear DNA molecules. As examples, the second amount could be of nuclear and mitochondrial DNA molecules or just the nuclear DNA molecules.

At block 2440, the normalized amount is compared to a reference value. As an example, the reference value could be a threshold value determined for normal samples. Block 2440 can be performed in a similar manner as block 1940 of method 1900. For example, the reference value can be determined from data of the type shown in FIGS. 20-23.

At block 2450, a classification of a level an auto-immune disease in the organism is determined based on the comparison. The test can be for a specific auto-immune disease, e.g., SLE. As examples, the classifications can include positive for the auto-immune disease, negative for the auto-immune disease, or indeterminate. Further examples can include whether the auto-immune diseases is active or inactive, as in FIGS. 20 and 22.

D. Size

Figure 25:
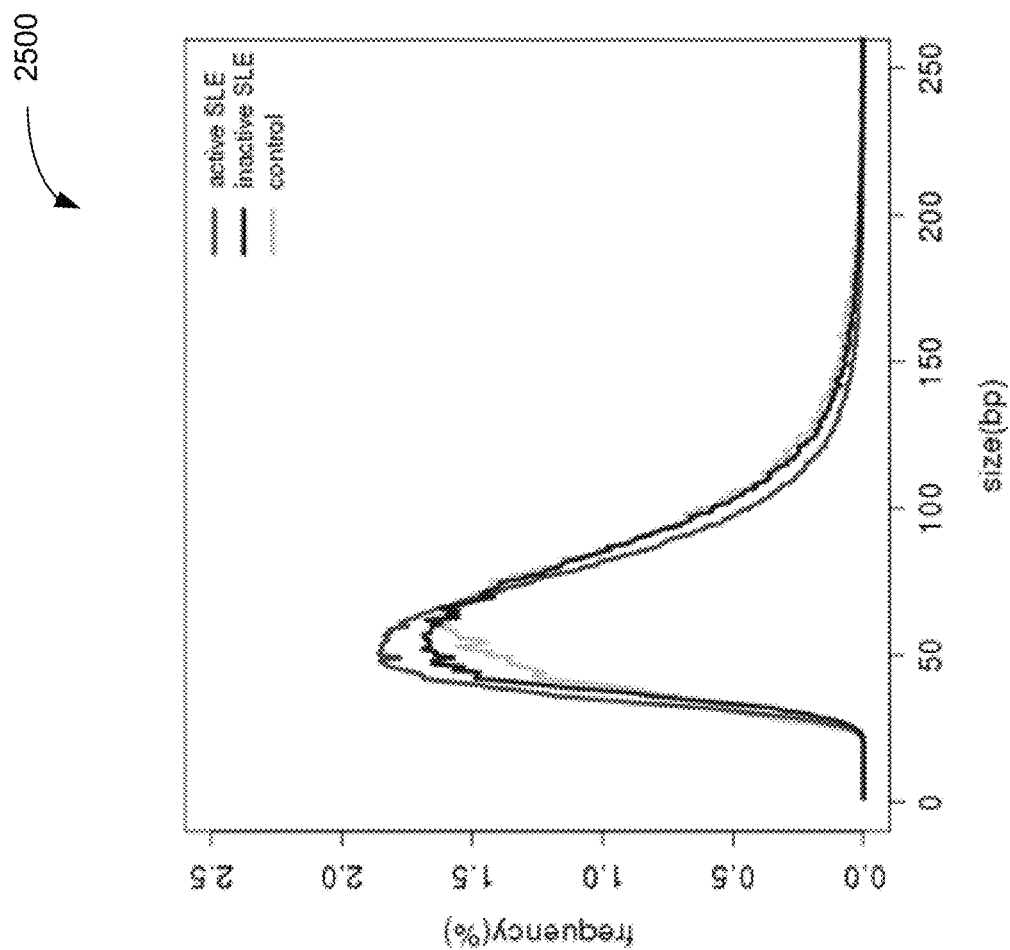
FIG. 25 is a plot 2500 showing size distributions of mitochondrial DNA (MtDNA) for various groups according to embodiments of the present invention.

FIG. 25 is a plot 2500 showing size distributions of mitochondrial DNA (MtDNA) for various groups according to embodiments of the present invention. The various groups are control groups, inactive SLE, and active SLE.

As one can see, the size distributions get smaller from control to inactive SLE, and even smaller for active SLE. This relationship can be used to identify whether a patient has no SLE, inactive SLE, or active SLE based on the size distributions. For example, a statistical value of an average, median, or mode (location of the peak) of the size distributions gets smaller for inactive SLE patients relative to healthy patients, and then even smaller for active SLE patients. Various statistical values can be used, such as a proportion of sequence reads below a specific size (e.g., 70 bp), a ratio of a number of sequence reads of two size (e.g., number at 60 by divided by number at 90 bp), or ratios of two other statistical values. All such statistical values would show a shift to smaller sizes. Other examples of suitable statistical sizes can be found in U.S. Pat. No. 8,620,593 and U.S. Patent Publication 2013/0237431, both of which are incorporated by reference.

Figure 26:
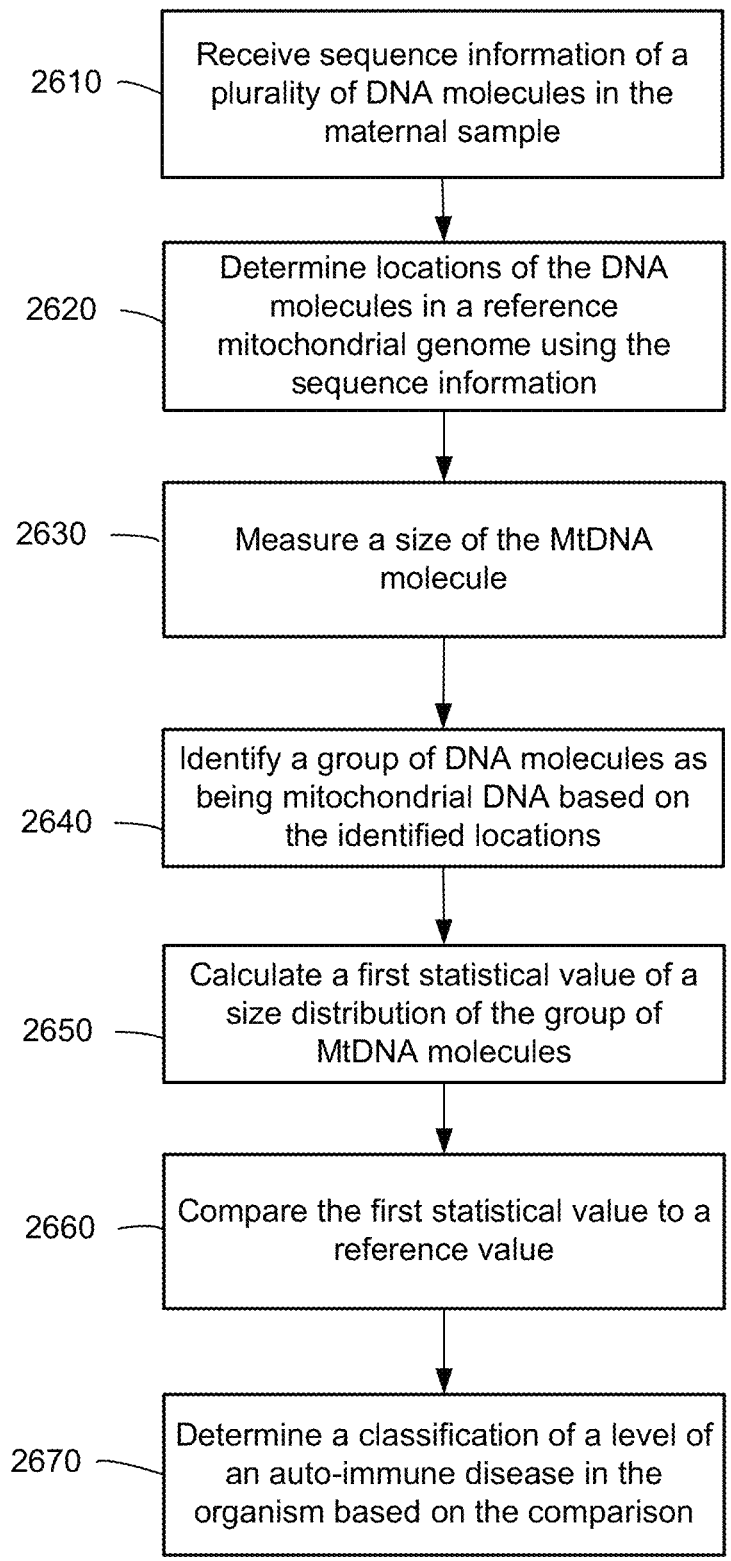
FIG. 26 is a flowchart illustrating a method 2600 of analyzing a biological sample of an organism to determine a classification of a level an auto-immune disease in the organism using sizes of MtDNA according to embodiments of the present invention.

FIG. 26 is a flowchart illustrating a method 2600 of analyzing a biological sample of an organism to determine a classification of a level an auto-immune disease in the organism using sizes of MtDNA according to embodiments of the present invention. The biological sample includes cell-free DNA.

At block 2610, sequence information of a plurality of DNA molecules in the biological sample is received at a computer system. Block 2610 can be performed in a similar manner as block 1110 of method 1100.

At block 2620, for each of a plurality of DNA molecules in the biological sample, a location of the DNA molecule in a reference mitochondrial genome is determined using the sequence information for the DNA molecule. As the location can provide whether the DNA molecule is nuclear DNA or mitochondrial DNA, only the mitochondrial DNA can be included as part of the plurality of DNA molecules. The location of the DNA molecule can be determined in a reference nuclear genome or a reference mitochondrial genome using the sequence information for the DNA molecule, e.g., by performing a mapping procedure of a sequence read to the reference nuclear genome and reference mitochondrial genome. Block 2620 can be performed in a similar manner as other location techniques described herein.

At block 2630, a size of the DNA molecule are measured using the determined location of the DNA molecule. Obtaining the size of a DNA molecule is described in U.S. Patent Publication 2013/0237431 entitled "Size-Based Analysis of Fetal DNA Fraction in Maternal Plasma" by Lo et al., the contents of which are incorporated herein by reference for all purposes.

At block 2640, a group of DNA molecules are identified as being mitochondrial DNA based on the determined locations. Once the group of MtDNA molecules has been identified, a size distribution of the group can be analyzed. The group can comprise all or just a portion of the plurality of DNA molecules whose locations were determined.

At block 2650, a first statistical value of a size distribution of the group of mitochondrial DNA molecules is calculated. As mentioned above, various statistical values can be used. In embodiments, the first statistical value may be determined by computing an area under a first curve at a specified size. The first curve may be a plot of a cumulative frequency of MtDNA molecules over a range of sizes. In one embodiment, the first statistical value can be an average, mean, or median size of the MtDNA fragments. In another embodiment, the first statistical value can include a sum of the length of fragments below a first size, which can be a type of cutoff. For example, each of the fragments that are smaller than 70 by can have their lengths summed. The sum can be divided by another number, such as a sum of the lengths of all MtDNA fragments or a sum of the lengths of fragments greater than a second size cutoff (which may be the same as the first size). For example, the first statistical value can be a ratio of the total length of fragments below a first size cutoff relative to a total length of fragments, or a ratio of the total length of small fragments relative to a total length of large fragments.

At block 2660, the first statistical value is compared to a reference value. In embodiments, the reference value may correspond to a reference statistical value of a size distribution from one or more reference samples, e.g., healthy control(s) or inactive SLE patient(s). The reference value may be determined by computing an area under a reference curve at the specified size. The reference curve may be a plot of cumulative frequency of MtDNA molecules for the one or more reference samples over the range of sizes. In various embodiments, a total size distribution from multiple reference samples can be used, or separate values from different size distributions can be combined to provide a single reference value.

At block 2670, a classification of a level an auto-immune disease in the organism is determined based on the comparison. Examples of classifications include no auto-immune disease, inactive auto-immune disease, and active auto-immune disease. The first statistical value and the reference value may be compared to obtain a separation value, which can be compared to a threshold (cutoff) to determine the classification. In one embodiment, the separation value can be a difference between the first statistical value and the reference value is determined. In another embodiment, the separation value can be a ratio of the first statistical value to the reference value.

The separation value may be a difference in the proportion of short MtDNA fragments between the test sample and one or more reference samples using the following equation:

$$\Delta F = P(\leq 150 bp)_{test} - P(\leq 150 bp)_{ref}$$

where $P(\leq 150\ bp)_{test}$ denotes the proportion of sequenced MtDNA fragments from the test test sample with sizes $\leq 150$ bp, and $P(\leq 150\ bp)_{ref}$ denotes the proportion of sequenced MtDNA fragments from the one or more reference samples with sizes $\leq 150$ bp. In other embodiments, other size thresholds can be used, for example, but not limited to 100 bp, 110 bp, 120 bp, 130 bp, 140 bp, 160 bp and 166 bp. In other embodiments, the size thresholds can be expressed in bases, or nucleotides, or other units.

The separation value may be compared to one or more cutoff values. A separation value can be compared to two cutoff values to determine whether the separation value is within a particular range. The range can include one cutoff to determine if a non-normal data point occurs (e.g. existence of the auto-immune disease), and a second cutoff could be used to determine if the data point is for an active or inactive status for the auto-immune disease.

In some embodiments, the first statistical value can be compared to a plurality of reference values to determine the classification of the level of the auto-immune disease. For example, the auto-immune disease can be determined to be active when the first statistical value is greater than a first reference value, e.g., 0.055 as mentioned for FIG. 22. The auto-immune disease can be determined to be inactive when the first statistical value is less than the first reference value and greater than a second reference value (e.g., 0.18 with reference to FIGS. 20 and 22). The auto-immune disease can be determined to not exist when the first statistical value is less than the second reference value.

V. Non-Hematopoietic Tissue

Different cell types contain different numbers of mitochondrial DNA. If there is a tissue that contains a higher amount of mitochondrial DNA per cell than the average for the hematopoietic cells, an elevation in the plasma mitochondrial DNA % is seen if that plasma sample contains DNA released from that other tissue. For example, FIG. 5 showed that chorionic villus cells (first trimester placental tissues) have higher mitochondrial DNA content than the buffy coat, which explains a higher plasma MtDNA % in the first trimester samples in FIG. 3. Further, higher MtDNA % was seen in cancer patients. Accordingly, a normalized amount of MtDNA in a samples can be used to estimate a concentration of DNA in the biological sample derived from a non-hematopoietic tissue source. And, when an elevated MtDNA % is detected, cell death in some non-hematopoietic tissues (e.g., signifying some pathology) can be identified.

Figure 27:
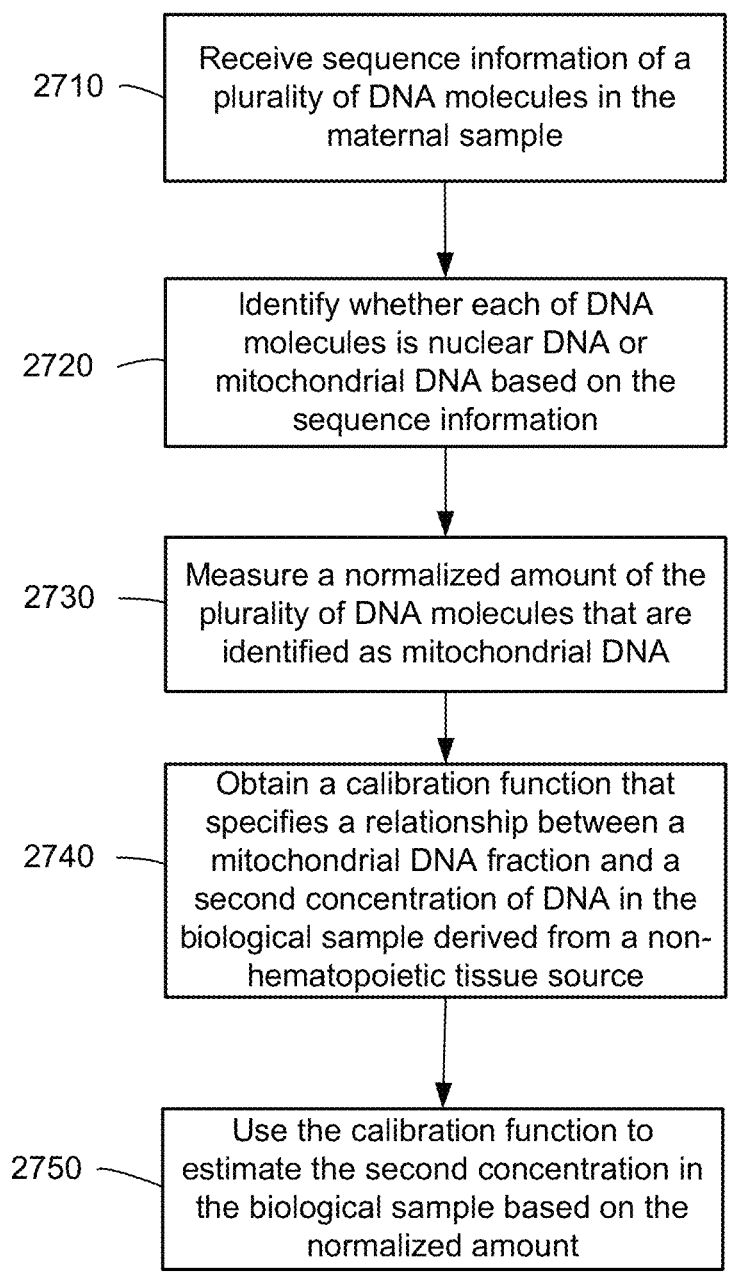
FIG. 27 is a flowchart illustrating a method 2700 of analyzing a biological sample of a female subject pregnant with a fetus to estimate a concentration of DNA in the biological sample derived from a non-hematopoietic tissue source according to embodiments of the present invention.
Figure 28:
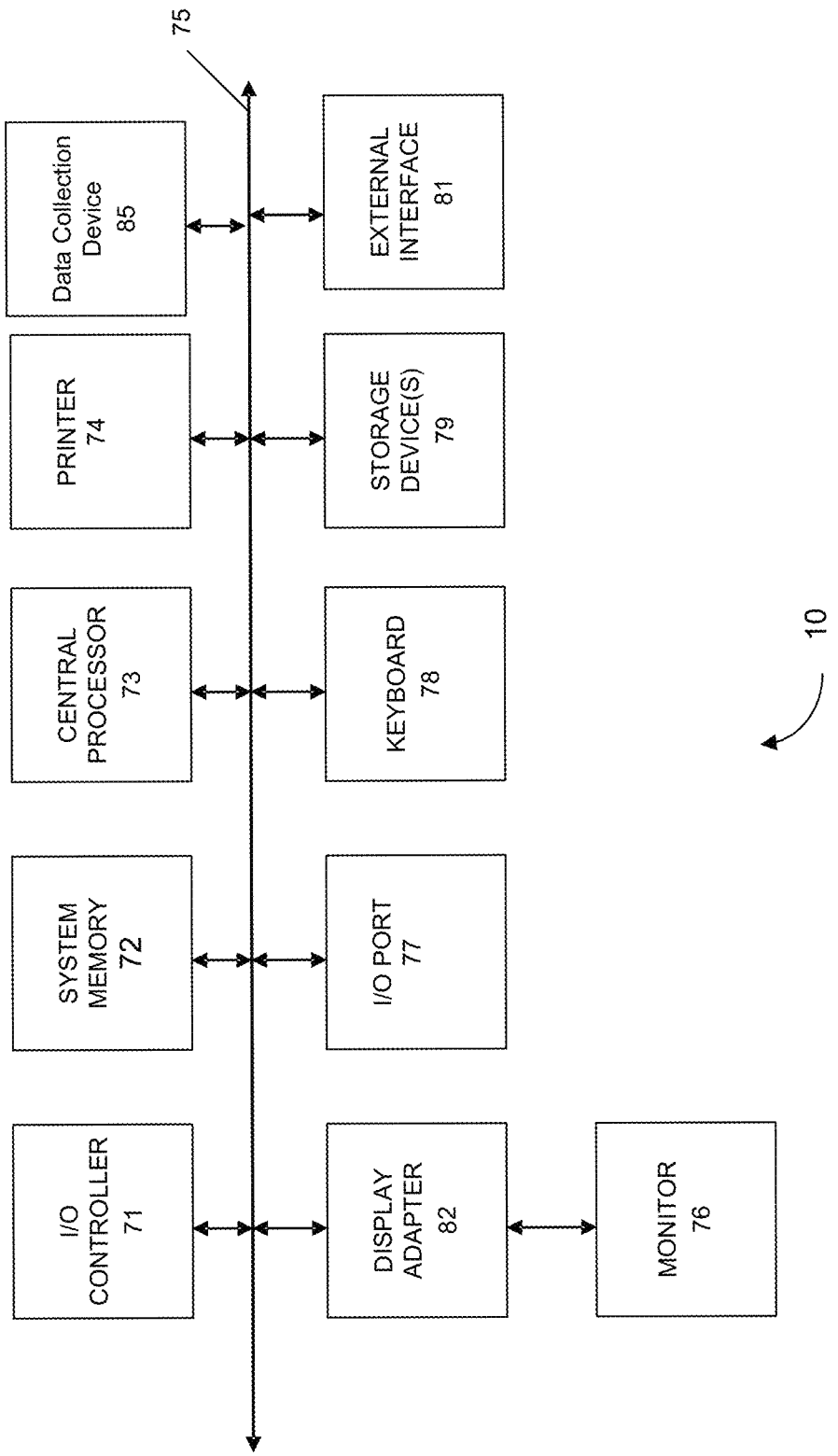
FIG. 28 shows a block diagram of an example computer system 10 usable with system and methods according to embodiments of the present invention.

FIG. 27 is a flowchart illustrating a method 2700 of analyzing a biological sample of a female subject pregnant with a fetus to estimate a concentration of DNA in the biological sample derived from a non-hematopoietic tissue source according to embodiments of the present invention. The biological sample includes cell-free DNA. The cell-free DNA of the biological sample include mitochondrial DNA and nuclear DNA. As examples, the biological sample can be plasma or serum.

At block 2710, sequence information of a plurality of DNA molecules in the biological sample is received at a computer system. Block 2710 can be performed in a similar manner as block 1110 of method 1100.

At block 2720, for each of a plurality of DNA molecules in the biological sample, it is determined whether the DNA molecule is nuclear DNA or mitochondrial DNA. The location of the DNA molecule can be determined in a reference nuclear genome or a reference mitochondrial genome using the sequence information for the DNA molecule, e.g., by performing a mapping procedure of a sequence read to the reference nuclear genome and reference mitochondrial genome. Block 2720 can be performed in a similar manner as block 1120 of method 1100.

At block 2730, a normalized amount of the plurality of DNA molecules that are identified as mitochondrial DNA is measured. Block 2730 can be performed in a similar manner as block 1130 of method 1100. Accordingly, the normalized amount can be relative to a second amount of the plurality of DNA molecules including DNA molecules that are identified as nuclear DNA molecules. As examples, the second amount could be of nuclear and mitochondrial DNA molecules or just the nuclear DNA molecules.

At block 2740, a calibration function that specifies a relationship between a mitochondrial DNA concentration and a second concentration of DNA in the biological sample derived from a non-hematopoietic tissue source is obtained. Block 2740 can be performed in a similar manner as block 1140 of method 1100.

At block 2750, the calibration function is used to estimate the second concentration in the biological sample based on the normalized amount. Block 2750 can be performed in a similar manner as block 1150 of method 1100.

In various embodiments, the non-hematopoietic tissue source can include a liver, a lung, a heart, a brain, a non-hematopoietic cancer, or a placenta. For example, the second concentration of DNA can be monitored over time to track a size of a tumor, e.g., as discussed for FIG. 16. Thus, the size of the tumor can be tracked by determining a fractional concentration of mitochondrial DNA in cells of the tumor and determining the size of the tumor based on the fractional concentration of mitochondrial DNA in cells of the tumor.

VI. Materials and Methods for Fetal Analysis

Below are some example techniques used in the fetal analysis. Other embodiments can use different techniques.

For the preparation of plasma and buffy coat samples, peripheral blood samples were centrifuges at 1,600 g for 10 min at 4° C. (Centrifuge 5810 R, Eppendorf). After this first round of centrifugation, the upper clear layer is the plasma portion, was transferred to a 2 mL centrifuge tubes and re-centrifuged at 16,000 g for 10 min at 4° C. (Centrifuge 5417 R, Eppendorf) (Chiu et al. 2001). Buffy coat was the intermediate layer and was transferred to a 1.5 mL centrifuge tube, re-centrifuged at 2,500 g for 5 min at room temperature (Microlitre Centrifuge Z 233 M-2, Hermle) to remove any residual plasma. Both cell-free plasma and buffy coat were stored in microcentrifuge tubes at −80° C.

For plasma DNA extraction, plasma DNA was extracted with the QIAamp DSP DNA Blood Mini Kit (Qiagen) following the manufacturer's vacuum protocol with some modifications. Each 400 µL of plasma was mixed with 40 µL of protease and 400 µL of Buffer AL. The mixture was incubated for 20 min at 56° C. 400 µL of ice-cold absolute ethanol was mixed thoroughly with the lysate. The lysate was flowed through the QIAamp Mini spin column. Each column was used with not more than 2 mL of plasma being applied. After the lysate has been drawn through the column, it was washed by 600 µL Buffer AW1 and followed by Buffer AW2. The column was spun at 16,000 g for 3 min after the washing step to remove all the residual washing buffer. 70 µL of deionized water was added to each column and incubated for 5 min at room temperature. The column was then centrifuged at 16,000 g for 1 min to elute the DNA. The extracted DNA was stored at −30° C. for subsequent experiments.

For genomic DNA extraction from buffy coat, genomic DNA was extracted from buffy coat using QIAamp DNA Blood Mini Kit (Qiagen) following the Blood or Body Fluid Spin protocol. For each sample, 400 µL of buffy coat was mixed with 40 µL of protease and 400 µL of Buffer AL. The mixture was incubated for 20 min at 56° C. After incubation, 400 µL of ice-cold absolute ethanol was mixed thoroughly with the lysate. 600 µL of the lysate was then applied to the QIAamp Mini spin column and centrifuged at 6,000 g for 1 min at room temperature. This procedure repeated until all the lysate flowed through the column. Then the column was then washed by 600 µL of Buffer AW1 and AW2. After the washing, the column was centrifuged at 16,000 g for 3 min to remove all the residual washing buffer. Lastly, 80 µL of deionized water was added to the column and incubated for 5 min at room temperature. Genomic DNA was eluted by centrifuging the column at 16,000 g for 1 min.

For genomic DNA extraction from chorionic villus sampling (CVS) and placenta tissue, QIAamp DNA Mini Kit (Qiagen) was used for genomic DNA extraction from CVS and placental tissue. DNA Purification from Tissues Spin Protocol was used with minor modifications. Placenta and CVS tissues were washed twice with phosphate-buffered saline (PBS) and cut into small pieces. Each sample was mixed with 360 µl of Buffer ATL and 40 µL of proteinase K for 5 hour incubation at 56° C. with gentle shaking until the whole tissue was digested. 400 µL of Buffer AL was added and incubated at 70° C. for 15 min. It is followed by adding 400 µL of cold absolute ethanol for DNA precipitation. The reaction mix was then running through the QIAamp Mini spin column. 600 µL of wash buffer AW1 and AW2 were added according. The column was centrifuged at 16,000 g for 3 min after the washing step to remove all the residual washing buffer. The column was centrifuged at 16,000 g for 3 min after the washing step to remove all the residual washing buffer. Lastly, DNA from the placenta and CVS were eluted in 100 µL and 30 µL of deionized water respectively.

For genomic DNA quantification, extracted genomic DNA was quantified by NanoDrop 2000 spectrophotometer (Thermo Scientific) by measuring the ratio of absorbance at 260 nm and 280 nm (260/280).

For genomic DNA sonication, 5 µg of genomic DNA was diluted into 130 µl of ultra-pure water and sonicated by S220 Focused-ultrasonicator (Covaris) to size range from 100-300 bp following manufacture's instruction before proceeding to library preparation.

For plasma DNA library preparation, plasma DNA libraries were prepared by using the KAPA Library Preparation Kit (Kapa Biosystems) for a pair-end protocol. End-repair reaction was the first step, carried out with 85 μL of plasma DNA. 10 μL of 10× End Repair Buffer, 5 μL of End Repair Enzyme Mix. The final reaction mix volume is 100 μL. After incubating at 20° C. for 30 min, the reaction mix was purified by using MinElute Reaction Cleanup Kit (Qiagen) following manufacture's instruction and eluted in 31 μL of EB buffer. The eluted product was 30 μL of end-repaired DNA was mixed with 5 μL of 10× A-Tailing Buffer, 3 μL of A-Tailing Enzyme and 12 μL of ultra-pure water to give a total 50μL reaction mix. The mix was incubated at 30° C. for 30 min and followed by MinElute Reaction Cleanup Kit (Qiagen) for purification. The A-tailed DNA was eluted with 31 μL of Buffer EB and proceeded to adapter ligation. The 30 μL of A-tailed DNA was mixed with 10 μL of 5× Ligation Buffer, 5 μL of DNA Ligase, 1 μL of DNA Adaptor (PE multiplex, 15 μM), and 4 μL of ultra-pure water to for a 50 μL reaction. The reaction was incubated at 20° C. for 15 in and followed by MinElute Reaction Cleanup Kit (Qiagen) for purification. DNA was eluted in 23 μL of EB Buffer for the next PCR amplification. The PCR enrichment reaction mix included 22 μL of adaptor ligated DNA, 25 μL of 2× KAPA HiFi HotStart ReadyMix, 500 nM of PE PCR Primer InPE 1.0, 10 nM of PE PCR Primer InPE 2.0, and 500 nM of PCR Primer Index. The PCR profile was as follow: DNA denaturation at 98° C. for 45 sec, 14 cycles of 98° C. for 15 sec, 65° C. for 30 sec, and 72° C. for 30 sec, final extension at 72° C. for 1 min. PCR product was kept at 4° C. until proceeded to PCR purification by MinElute PCR Purification Kit (Qiagen) following manufacturer's instruction. The final library was eluted with 25 μL of Buffer EB and ready for DNA library validation.

For genomic DNA library preparation, genomic DNA libraries were prepared by using the KAPA Library Preparation Kit (Kapa Biosystems) for a pair-end protocol. 1 μg of sonicated genomic DNA was diluted into 85 μL of ultra-pure water. In end-repair reaction, 85 μL of sonicated DNA, 10 μL of 10× End Repair Buffer, 5 μL of End Repair Enzyme Mix were added together. The final reaction mix volume is 100 μL. After incubating at 20° C. for 30 min, the reaction mix was purified by using MinElute Reaction Cleanup Kit (Qiagen) following manufacture's instruction and eluted in 31 μL of EB buffer. The eluted product was 30 μL of end-repaired DNA was mixed with 5 μL of 1 Ox A-Tailing Buffer, 3 μL of A-Tailing Enzyme and 12 μL of ultra-pure water to give a total 50 μL reaction mix. The mix was incubated at 30° C. for 30 min and followed by MinElute Reaction Cleanup Kit (Qiagen) for purification. The A-tailed DNA was eluted with 31 μL of Buffer EB and proceeded to adapter ligation. The 30 μL of A-tailed DNA was mixed with 10 μL of 5× Ligation Buffer, 5 μL of DNA Ligase, 1 μL of DNA Adaptor (PE multiplex, 15 μM), and 4 μL of ultra-pure water to for a 50 μL reaction. The reaction was incubated at 20° C. for 15 in and followed by MinElute Reaction Cleanup Kit (Qiagen) for purification. DNA was eluted in 23 μL of EB Buffer for the next PCR amplification. The PCR enrichment reaction mix included 22 μL of adaptor ligated DNA, 25 μL of 2× KAPA HiFi HotStart ReadyMix, 500 nM of PE PCR Primer InPE 1.0, 10 nM of PE PCR Primer InPE 2.0, and 500 nM of PCR Primer Index. The PCR profile was as follow: DNA denaturation at 98° C. for 45 sec, 12 cycles of 98° C. for 15 sec, 65° C. for 30 sec, and 72° C. for 30 sec, final extension at 72° C. for 1 min. PCR product was kept at 4° C. until proceeded to PCR purification by MinElute PCR Purification Kit (Qiagen) following manufacturer's instruction. The final library was eluted with 25 μL of Buffer EB and ready for DNA library validation.

Library size distributions were analyzed using DNA 1000 Kit with a 2100 Bioanalyzer (Agilent) following manufacturer's protocol. For plasma DNA library, the typical size was 290 bp.

DNA libraries were quantified by a SYBR Green real-time qPCR assay using the KAPA Library Quantification Kit-Illumina/ABI Prism SYBR Green (Kapa Biosystems) on a 7300 Real-Time PCR system (Applied Biosystems). The kit contains primers that can amplify DNA library fragments by flanking the Illumina adapter sequences. Standard curve of the kit is made of 6 standards in 10-folds dilution, ranging from 20 pM to 0.0002 pM. The reaction volume was 20 μL, consisting of 4 μL of standard or 100,000-fold diluted DNA library, 12 μL of KAPA SYBR FAST qPCR Master Mix with Primer Premix and 4 μL of PCR-graded water. Each sample was done in duplicate and 6 NTCs were included for contamination detection. The PCR profile was 95° C. for 10 min; 35 cycles of 95° C. for 30 s and 60° C. for 45 s. The concentration of the libraries was calculated according this formula by taking into account for the size difference between the DNA Standard (452 bp) and average size of DNA library:

$$\text{Library stock concentration} = \frac{\text{Mean concentration from duplicate } (pM) \times \text{Dilution factor} \times 452}{\text{Average library size from Bioanalyzer}}$$

For DNA sequencing and alignment, DNA libraries were sequenced using a standard paired-end (76 bp×2 cycles) protocol. Additional 7 sequencing cycles were used to decode the index sequence of each DNA molecule in multiplex sequencing on a HiSeq 2500 or HiSeq 2000 sequencer (Illumina). A non-repeat-masked hg19 reference human genome (genome.ucsc.edu) using the Short Oligonucleotide Alignment Program 2 (SOAP2) (soap.genomics.org.cn) was applied for sequence reads alignment. Only paired-end reads with both ends aligned to same chromosome with correct orientation, spanning and insert size of =<600 by were used. Reads with no more than two nucleotide mismatches were allowed for each member of the paired-end reads. Only reads mapped to a unique genomic location were used for the downstream analysis.

VII. Computer System

Any of the computer systems mentioned herein may utilize any suitable number of subsystems. Examples of such subsystems are shown in FIG. 6 in computer apparatus 10. In some embodiments, a computer system includes a single computer apparatus, where the subsystems can be the components of the computer apparatus. In other embodiments, a computer system can include multiple computer apparatuses, each being a subsystem, with internal components. A computer system can include desktop and laptop computers, tablets, mobile phones and other mobile devices.

The subsystems shown in FIG. 6 are interconnected via a system bus 75. Additional subsystems such as a printer 74, keyboard 78, storage device(s) 79, monitor 76, which is coupled to display adapter 82, and others are shown. Peripherals and input/output (I/O) devices, which couple to I/O controller 71, can be connected to the computer system by any number of means known in the art such as input/output (I/O) port 77 (e.g., USB, FireWire®). For example, I/O port 77 or external interface 81 (e.g. Ethernet, Wi-Fi, etc.) can be used to connect computer system 10 to a wide area network such as the Internet, a mouse input device, or a scanner. The interconnection via system bus 75 allows the central processor 73 to communicate with each subsystem and to control the execution of a plurality of instructions from system memory 72 or the storage device(s) 79 (e.g., a fixed disk, such as a hard drive, or optical disk), as well as the exchange of information between subsystems. The system memory 72 and/or the storage device(s) 79 may embody a computer readable medium. Another subsystem is a data collection device 85, such as a camera, microphone, accelerometer, and the like. Any of the data mentioned herein can be output from one component to another component and can be output to the user.

A computer system can include a plurality of the same components or subsystems, e.g., connected together by external interface 81 or by an internal interface. In some embodiments, computer systems, subsystem, or apparatuses can communicate over a network. In such instances, one computer can be considered a client and another computer a server, where each can be part of a same computer system. A client and a server can each include multiple systems, subsystems, or components.

It should be understood that any of the embodiments of the present invention can be implemented in the form of control logic using hardware (e.g. an application specific integrated circuit or field programmable gate array) and/or using computer software with a generally programmable processor in a modular or integrated manner. As used herein, a processor includes a single-core processor, multi-core processor on a same integrated chip, or multiple processing units on a single circuit board or networked. Based on the disclosure and teachings provided herein, a person of ordinary skill in the art will know and appreciate other ways and/or methods to implement embodiments of the present invention using hardware and a combination of hardware and software.

Any of the software components or functions described in this application may be implemented as software code to be executed by a processor using any suitable computer language such as, for example, Java, C, C++, C#, Objective-C, Swift, or scripting language such as Perl or Python using, for example, conventional or object-oriented techniques. The software code may be stored as a series of instructions or commands on a computer readable medium for storage and/or transmission, suitable media include random access memory (RAM), a read only memory (ROM), a magnetic medium such as a hard-drive or a floppy disk, or an optical medium such as a compact disk (CD) or DVD (digital versatile disk), flash memory, and the like. The computer readable medium may be any combination of such storage or transmission devices.

Such programs may also be encoded and transmitted using carrier signals adapted for transmission via wired, optical, and/or wireless networks conforming to a variety of protocols, including the Internet. As such, a computer readable medium according to an embodiment of the present invention may be created using a data signal encoded with such programs. Computer readable media encoded with the program code may be packaged with a compatible device or provided separately from other devices (e.g., via Internet download). Any such computer readable medium may reside on or within a single computer product (e.g. a hard drive, a CD, or an entire computer system), and may be present on or within different computer products within a system or network. A computer system may include a monitor, printer, or other suitable display for providing any of the results mentioned herein to a user.

Any of the methods described herein may be totally or partially performed with a computer system including one or more processors, which can be configured to perform the steps. Thus, embodiments can be directed to computer systems configured to perform the steps of any of the methods described herein, potentially with different components performing a respective steps or a respective group of steps. Although presented as numbered steps, steps of methods herein can be performed at a same time or in a different order. Additionally, portions of these steps may be used with portions of other steps from other methods. Also, all or portions of a step may be optional. Additionally, any of the steps of any of the methods can be performed with modules, circuits, or other means for performing these steps.

The specific details of particular embodiments may be combined in any suitable manner without departing from the spirit and scope of embodiments of the invention. However, other embodiments of the invention may be directed to specific embodiments relating to each individual aspect, or specific combinations of these individual aspects.

The above description of example embodiments of the invention has been presented for the purposes of illustration and description. It is not intended to be exhaustive or to limit the invention to the precise form described, and many modifications and variations are possible in light of the teaching above.

A recitation of "a", "an" or "the" is intended to mean "one or more" unless specifically indicated to the contrary. The use of "or" is intended to mean an "inclusive or," and not an "exclusive or" unless specifically indicated to the contrary.

All patents, patent applications, publications, and descriptions mentioned herein are incorporated by reference in their entirety for all purposes. None is admitted to be prior art.

What is claimed is:

1. A method of analyzing a biological sample of an organism that is human, the biological sample including DNA molecules originating from normal cells and potentially from cells associated with a non-hematopoietic cancer, the biological sample including cell-free DNA, the cell-free DNA including mitochondrial DNA and nuclear DNA, wherein the biological sample is plasma or serum, the method comprising:

performing massively parallel sequencing of a plurality of DNA molecules that are cell-free from the biological sample of the organism to obtain sequence reads, the plurality of DNA molecules including nuclear DNA molecules and mitochondrial DNA molecules, wherein the sequence reads are at least 30 bases long;

receiving, at a computer system, the sequence reads from the massively parallel sequencing of the plurality of DNA molecules that are cell-free from the biological sample of the organism;

for each of the plurality of DNA molecules:
determining, by the computer system, a location of the DNA molecule in a reference human nuclear genome or a reference human mitochondrial genome by mapping a corresponding sequence read to the reference human nuclear genome or to the reference human mitochondrial genome; and identifying, by the computer system, the DNA molecule is a nuclear DNA molecule or a mitochondrial DNA molecule based on the location, the plurality of DNA molecules including at least 500,000 DNA molecules;

determining, by the computer system, a normalized amount of the plurality of DNA molecules that are identified as mitochondrial DNA molecules, the normalized amount being relative to a second amount of the plurality of DNA molecules including DNA molecules that are identified as nuclear DNA molecules;

comparing the normalized amount to a reference value; and determining a classification of a level of the non-hematopoietic cancer in the organism based on the comparison, wherein the classification includes whether the non-hematopoietic cancer exists, a stage of the non-hematopoietic cancer, a size of a tumor, or a measure of a severity of the non-hematopoietic cancer.

2. The method of claim 1, wherein the classification of the level of the non-hematopoietic cancer includes whether metastasis has occurred.

3. The method of claim 1, wherein the normalized amount is compared to a plurality of reference values to determine the classification of the level of the non-hematopoietic cancer.

4. The method of claim 3, wherein the plurality of reference values are part of a calibration function that provides the size of the tumor as the classification.

5. The method of claim 1, further comprising performing, by the computer system:

determining a first amount of the plurality of DNA molecules that are mitochondrial DNA molecules;

determining the second amount of the plurality of DNA molecules by counting the nuclear DNA molecules; and computing a ratio of the first amount and the second amount, wherein the normalized amount of the plurality of DNA molecules that are identified as mitochondrial DNA molecules is determined using the ratio.

6. The method of claim 1, wherein the mapping includes:

performing a first mapping procedure using one or more first criteria for determining a first alignment to the reference human mitochondrial genome; and for each sequence read that is determined to align to the reference human mitochondrial genome based on the first mapping procedure:

performing a second mapping procedure to the reference human nuclear genome and to the reference human mitochondrial genome using one or more second criteria that are more stringent than the one or more first criteria, wherein a sequence read contributes to the normalized amount only if the sequence read maps to the reference human mitochondrial genome for the first mapping procedure and the second mapping procedure.

7. The method of claim 6, wherein the one or more second criteria include that the sequence read maps to a unique position on the reference human mitochondrial genome.

8. The method of claim 6, wherein the one or more second criteria include that the sequence read aligns to the reference human mitochondrial genome with fewer mismatches than a second alignment to the reference human nuclear genome.

9. The method of claim 1, wherein mapping the DNA molecules uses at least a majority of the reference human nuclear genome and the reference human mitochondrial genome.

10. The method of claim 1, wherein the non-hematopoietic cancer is a hepatocellular carcinoma or a nasopharyngeal cancer.

11. The method of claim 1, wherein the normalized amount of the plurality of DNA molecules that are identified as mitochondrial DNA molecules corresponds to a concentration of mitochondrial DNA in the biological sample.

12. The method of claim 1, wherein the massively parallel sequencing is a random sequencing of the plurality of DNA molecules from the biological sample of the organism.

13. The method of claim 1, further comprising:

treating the organism for cancer in response to the classification of the level of the non-hematopoietic cancer including an existence of cancer in the organism.

14. The method of claim 12, wherein the classification of the level of the non-hematopoietic cancer in the organism is determined after treating the organism for cancer.

15. The method of claim 1, further comprising:

outputting, by the computer system, the classification of the level of the non-hematopoietic cancer in the organism.

16. The method of claim 1, wherein the non-hematopoietic cancer is from non-hematopoietic cells that have higher number of mitochondria than hematopoietic cells do.

* * * * *